(12) United States Patent
Piazza et al.

(10) Patent No.: US 6,200,980 B1
(45) Date of Patent: Mar. 13, 2001

(54) METHOD OF TREATING A PATIENT HAVING PRECANCEROUS LESIONS WITH PHENYL PURINONE DERIVATIVES

(75) Inventors: Gary A. Piazza, Highlands Ranch, CO (US); Rifat Pamukcu, Spring House, PA (US)

(73) Assignee: Cell Pathways, Inc., Horsham, PA (US)

( * ) Notice: Subject to any disclaimer, the term of this patent is extended or adjusted under 35 U.S.C. 154(b) by 0 days.

(21) Appl. No.: 08/842,854

(22) Filed: Apr. 17, 1997

Related U.S. Application Data

(63) Continuation of application No. 08/472,804, filed on Jun. 7, 1995.

(51) Int. Cl.$^7$ .......................... A61K 31/505; A61K 31/52
(52) U.S. Cl. ......................... 514/258; 514/262; 514/266
(58) Field of Search ................................... 514/258, 262, 514/266

(56) References Cited

U.S. PATENT DOCUMENTS

| | | |
|---|---|---|
| 3,031,450 | 4/1962 | Fischer et al. . |
| 3,161,654 | 12/1964 | Shen . |
| 3,322,755 | 5/1967 | Roch et al. . |
| 3,517,005 | 6/1970 | Cronin et al. . |
| 3,594,480 | 7/1971 | Cronin et al. . |
| 3,647,858 | 3/1972 | Hinkley et al. . |
| 3,654,349 | 4/1972 | Shen et al. . |
| 3,780,040 | 12/1973 | Schettler et al. . |
| 3,812,127 | 5/1974 | Cronin et al. . |
| 3,819,631 | 6/1974 | Broughton et al. . |
| 3,920,636 | 11/1975 | Takahasi et al. . |
| 4,001,237 | 1/1977 | Partyka et al. . |
| 4,001,238 | 1/1977 | Partyka et al. . |
| 4,039,544 | 8/1977 | Broughton et al. . |
| 4,060,615 | 11/1977 | Matier et al. . |
| 4,079,057 | 3/1978 | Juby et al. . |
| 4,098,788 | 7/1978 | Crenshaw et al. . |
| 4,101,548 | 7/1978 | Crenshaw et al. . |
| 4,102,885 | 7/1978 | Crenshaw et al. . |
| 4,138,561 | 2/1979 | Crenshaw et al. . |
| 4,146,718 | 3/1979 | Jenks et al. . |
| 4,161,596 | 7/1979 | Kaplan et al. . |
| 4,171,363 | 10/1979 | Crenshaw et al. . |
| 4,208,521 | 6/1980 | Crenshaw et al. . |
| 4,209,623 | 6/1980 | Juby . |
| 4,423,075 | 12/1983 | Dvornik et al. . |
| 4,460,590 | 7/1984 | Möller . |
| 4,460,591 | 7/1984 | DeGraw et al. . |
| 4,880,810 | 11/1989 | Lowe, III et al. . |
| 4,885,301 | 12/1989 | Coates . |
| 4,923,874 | 5/1990 | McMahon et al. . |
| 4,950,680 | 8/1990 | Taylor et al. . |
| 5,073,559 | 12/1991 | Coates . |
| 5,147,875 | 9/1992 | Coates et al. . |
| 5,223,501 | 6/1993 | Chakravarty et al. . |
| 5,250,535 | 10/1993 | Verheyden et al. . |
| 5,272,147 | * 12/1993 | Bell et al. ............................ 514/258 |
| 5,346,901 | * 9/1994 | Bell et al. ............................ 514/258 |
| 5,358,952 | 10/1994 | Moschel et al. . |
| 5,401,774 | 3/1995 | Pamukcu et al. . |
| 5,439,895 | 8/1995 | Lee et al. . |
| 5,614,530 | 3/1997 | Kumar et al. . |
| 5,614,627 | 3/1997 | Takase et al. . |
| 5,696,159 | 12/1997 | Gross et al. . |

FOREIGN PATENT DOCUMENTS

| | | |
|---|---|---|
| 3038166 | 5/1981 | (DE) . |
| 0 347 146 A2 | 12/1989 | (EP) . |
| 0 349 239 A2 | 1/1990 | (EP) . |
| 0 351 058 | 1/1990 | (EP) . |
| 0 352 960 A2 | 1/1990 | (EP) . |
| 0 395 328 A2 | 10/1990 | (EP) . |
| 0 428 268 A2 | 5/1991 | (EP) . |
| 0 463 756 A1 | 1/1992 | (EP) . |
| 0 485 157 A2 | 5/1992 | (EP) . |
| 0 485 158 A2 | 5/1992 | (EP) . |
| 0 485 171 A2 | 5/1992 | (EP) . |
| 0 485 172 A2 | 5/1992 | (EP) . |
| 0 485 173 A2 | 5/1992 | (EP) . |
| 0 508 586 A1 | 10/1992 | (EP) . |
| 0 526 004 A1 | 2/1993 | (EP) . |
| 0 607 439 A1 | 7/1994 | (EP) . |
| 807826 | 1/1959 | (GB) . |
| 2063249 | 6/1981 | (GB) . |
| 56-53699 | 5/1981 | (JP) . |
| 57-167974 | 10/1982 | (JP) . |
| WO 92/03419 | 3/1992 | (WO) . |
| WO 93/07149 | 4/1993 | (WO) . |
| WO 93/12095 | 6/1993 | (WO) . |
| WO 94/05661 | 3/1994 | (WO) . |
| WO 95/19978 | 7/1995 | (WO) . |
| WO 97/03985 | 2/1997 | (WO) . |

OTHER PUBLICATIONS

Carter et al., Chemotherapy of Cancer, 2$^{nd}$ Ed., John Wiley & Sons, NY, NY, 1981, pp. 362–365.

Biddle, William et al., Antineoplastic Effect of the Pyrimido–Pyrimidine Derivative: RA 233, Pathologie Biologie, Jan., 1984, pp. 9–13.

Blaya, C. et al., Effect of the protein kinase inhibitors, 1–(5–isoquinolinylsulfonyl)–2–methylpiperazine H–7 and N–(2–[methylamino]ethyl)–5–isoquinoline–sulfonamide H–8 on Lewis lung carcinoma tumor progression, European Journal of Pharmacology, 354, pp. 99–104 (1998).

Chang, W. et al., Sulindac Sulfone Modulates the Expression and Cellular Localization of b–Catenin in Human Colon Carcinoma Cells, Digestive Disease Week, Apr. 1, 1999.

Earnest, D. et al., Piroxicam and Other Cyclooxygenase Inhibitors: Potential for Cancer Chemoprevention, Journal of Cellular Biochemistry, Supplement 161:156–166 (1992).

(List continued on next page.)

*Primary Examiner*—Jerome D. Goldberg
(74) *Attorney, Agent, or Firm*—Robert W. Stevenson

(57) ABSTRACT

Derivatives of Phenyl Purinone are useful for the treatment of patients having precancerous lesions. These compounds are also useful to inhibit growth of neoplastic cells.

8 Claims, No Drawings

OTHER PUBLICATIONS

Easwaran, V. et al., The Ubiquitin–Proteasome Pathway and Serine Kinase Activity Modulate Adenomatous Polyposis Coli Protein–mediated Regulation of β–Catenin–Lymphocyte Enhancer–binding Factor Signaling, The Journal of Biological Chemistry, vol. 274, No. 23, pp. 16641–16645, Jun. 4, 1999.

Jiang, X. et al., Inhibition of calmodulin–dependent phosphodiesterase induces apoptosis in human leukemic cells, Proc. Natl. Acad. Sci. USA, vol. 83, pp. 11236–11241, Oct. 1996.

Korinek, V. et al., Constitutive Transcriptional Activation by a β–Catenin–Tcf Complex in APC$^{-/-}$ Colon Carcinoma, Science, vol. 275, pp. 1784–1786, Mar. 21, 1997.

Mahmoud, N. et al., Apc Gene Mutation is Associated with a Dominant–Negative Effect upon Intestinal Cell Migration, Cancer Research 57, pp. 5045–5050, Nov. 15, 1997.

Mahmoud, N. et al., Genotype–Phenotype Correlation in Murine Apc Mutation: Differences in Enterocyte Migration and Response to Sulindac, Cancer Research 59, pp. 353–359, Jan. 15, 1999.

Morin, P. et al., Activation of β–Catenin–Tcf Signaling in Colon Cancer by Mutations in β–Catenin or APC, Science, vol. 275, pp. 1787–1789, Mar. 21, 1997.

Peifer, M., β–Catenin as Oncogene: The Smoking Gun, Science, vol. 275, pp. 1752–1753, Mar. 21, 1997.

Rubinfeld, B. et al., Stabilization of β–Catenin by Genetic Defects in Melanoma Cell Lines, Science, vol. 275, pp. 1790–1792, Mar. 21, 1997.

Waddell, W.R. et al., Am. J. Surgery, vol. 157, pp. 175–179 (1989).

Gonzaga, R.A.F. et al., The Lancet, Mar. 30, 1985, p. 751.

Waddell, W.R. et al., J. Surg. Oncology, vol. 24, pp. 83–87 (1983).

Federation Proceedings (1972) of the Federation of American Societies for Experimental Biology abstract Nos. 2044 and 2045.

Gilman, S.C. et al., Nonsteroidal Anti–inflammatory Drugs in Cancer Therapy, (circa 1985).

Brogden, R.N. et al., Drugs, vol. 16, pp. 97–114 (1978).

Hucker, H.B. et al., Drug Metabolism & Disposition, vol. 1, No. 6, pp. 721–736 (1973).

Shen, T.Y. et al., Chemical and Biological Studies on Indomethacin, Sulindac and Their Analogs, pp. 107–178 (circa 1975).

Duggan, D.E. et al., Clin. Pharm. & Therapeutics, vol. 21, No. 3, pp. 326–335 (1976).

Duggan, D.E. et al., J. Pharm. & Exper. Therap., vol. 201, No. 1, pp. 8–13 (1977).

Glavin, G.B. et al., Toxicology and Applied Pharmacology, vol. 83, pp. 386–389 (1986).

Moorghen, M. et al., Journal of Pathology, vol. 156, pp. 341–347 (1988).

Moorghen, M. et al., Acta Histochemica, Suppl.–Band XXIX, S. 195–199 (1990).

Bjarnason et al., Gastroenterology, vol. 94, No. 4, pp. 1070–1074 (1988).

Badrieh, Y., et al., Chem. Ber., vol. 125, pp. 667–674 (1992).

Silvola, J. et al., Effects of nonsteroidal anti–inflammatory drugs on rat gastric mucosal phosphodiesterase activity, Agents and Actions, vol. 12.4, pp. 516–520 (1982).

Curtis–Prior, P.B. et al., Cyclic Nucleotide Phosphodiesterase Activity of Human Normal and Carcinomatous Lung Tissue, The Lancet, pp. 1225–1225 Dec. 4, 1976.

Pepin, P. et al., Effects of Sulindac and Oltipraz on the tumorigenicity of 4–(methylnitrosamino)1–(3–pyridyl)–1–Butanone in A/J mouse lung, Carcinogenesis, vol. 13, No. 3, pp. 341–348 (1992).

Nicholson, C.D. et al. Differential modulaiton of tissue function and therapeutic potential of selective inhibitors of cyclic nucleotide phosphodiesterase isoenzymes, Trends Pharmacol. Sci. (TiPS), vol. 12, pp. 19–27 (1991).

Ahn, H.S. et al., Effects of Selective Inhibitors on Cyclic Nucleotide Phosphodiesterases of Rabbit Aorta, Biochemical Pharmacology, vol. 38, No. 19, pp. 3331–3339 (1989).

Luginer, C. et al., Selective Inhibition of Cyclic Nucleotide Phosphodiesterases of Human, Bovine and Rat Aorta, Biochem. Pharmacology, vol. 35, No. 10, pp. 1743–1751 (1986).

Turner, N.C. et al., Relaxation of guinea–pig trachea by cyclic AMP phosphodiesterase inhibitors and their enhancement by sodium mitroprusside, Br. J. Pharmacol. vol. III, pp. 1047–1052 (1994).

Weishaar, R.E. et al., Multiple Molecular Forms of Cyclic Nucleotide Phosphodiesterase in Cardiac and Smooth Muscle and In Platelets, Biochem. Pharmacology, vol. 35, No. 5, pp. 787–800 (1986).

Murray, K.J. et al., Potential Use of Selective Phosphodiesterase Inhibitors in the Treatment of Asthma, New Drugs for Asthma Therapy, Birkhauser Verlag Basel, pp. 27–46 (1991).

Saeki, T. et al., Isolation of Cyclic Nucleotide Phosphodiesterase Isozymes From Pig Aorta, Biochem. Pharmacology, vol. 46, No. 5, pp. 833–839 (1993).

Turner, N.C. et al., Pulmonary effects of type V cyclic GMP specific phosphodiesterase inhibition in anaesthetized guinea–pig, Br. J. Pharmacol., vol. 111, 1198–1204 (1994).

Ferreira, S.H. et al., The molecular mechanism of action of peripheral morphone analgesia: stimulation of the cGMP system via nitric oxide release, European Journal of Pharmacology, 201 pp. 121–122 (1991).

Hidaka, H. et al., Selective Inhibitors of Three Forms of Cyclic Nucleotide Phosphodiesterase—Basic and Potential Clinical Applications, vol. 16, Advances in Cyclic Nucleotide and Protein Phosphorylation Research, pp. 245–259 (1984).

Tulshian, D. et al., Synthesis and Phosphodiesterase Activity of Carboxylic Acid Mimetics of Cyclic Guanosine 3", 5"–Monophosphate, J. Med. Chem, vol. 36, 1210–1220 (1993).

Yasumoto, T. et al., Properties of Base–Substituted and Carboxyl–Esterified Analogues of Griseolic Acid, a Potent cAMP Phosphodiesterase Inhibitor, Biochemical Pharmacology, vol. 43, No. 10, pp. 2073,2081 (1992).

Broughton, B.J. et al., Antiallergic Activity of 2–Phenyl–8–azapruin–6–ones, Journal of Medicinal Chemistry, vol. 18, No. 11, pp. 1117–1118 (1975).

Kodama, K. et al., Effects of a novel, selective and potent phosphodiesterase type V inhibitor, E4021, on myocardial ischemia in guinea pigs, Euro. J. of Pharma. 263, pp. 93–99 (1994).

Zacharski, L. R. et al., Effect of Mopidamol on Survival in Carcinoma of the Lung and Colon: Final Report of Veterans Administration Cooperative Study No. 188, J. of the Nat'l. Cancer Inst., vol. 80, No. 2, pp. 90–96 (1988).

Lichtner, R. B. et al., The Pyrimido–pyrimidine Derivatives RA 233 adn RX–RA 85 affect Growth and Cytoskeletal Organization of Rat Mammary Adenocarcinoma Cells, Eur. J. Cancer Clin. Oncol., vol. 23, No. 9, pp. 1269–1275 (1987).

Janik, P. et al., Inhibition of Growth of Primary and Metastatic Lewis Lung Carcinoma Cells by the Phosphodiesterase Inhibitor Isobutylmethylxanthine, Cancer Res. vol. 40, pp. 1950–1954, (Jun., 1980).

Bergstrand, Hakan et al., Effects of Antiallergic Agents, Compound 48/80, and Some Reference Inhibitors on the Activity of Partially Purified Human Lung Tissue Adenosine Cyclic 3',5'–Monophosphate and Guanosine Cyclic 3',5'–Monophosphate Phosphodiesterases, Molecular Pharmacology, 13, pp. 38–43 (1976).

Drees, Markus et al., 3',5'–Cyclic Nucleotide Phosphodiesterase in Tumor Cells as Potential Target for Tumor Growth Inhibition, Cancer Research 53, pp. 3058–3061 (1993).

Semmler, J. et al., Xanthine derivatives: comparison between suppression of tumor necrosis factor–x production and inhibition of cAMP phosphodiesterase activity, Immunology 78, pp. 520–525 (1993).

Mehta, Rajendra et al., Structure–Activity Relationships of Brassinin in Preventing the Development of Carcinogen–Induced Mammary Lesions in Organ Culture, Anticancer Research 14: 1209–1214 (1994).

Makaryan, A.P. et al., Cyclic Nucleotides in Patients with Malignant Neoplasms of the Colon, Laboratornoe Delo, vol. 8, pp. 31–33 (1991).

Clarke, W.R. et al., The type III phosphodiesterase inhibitor milrinone and type V PDE inhibitor dipyridamole individually and synergistically reduce elevated pulmonary vascular resistance (Abstract Only), Pulm. Pharmacol., 7(2), pp. 81–89, (1994).

Raeburn, David et al., Effects of isoenzyme–selective inhibitors of cyclic nucleotide phosphodiesterase on microvascular leak in guinea pig airways in vivo (Abstract Only), J. Pharmacol. Exp. Ther., 267(3), pp. 1147–1151 (1993).

Marcoz, P. et al., Modulation of rat thymocyte proliferative response through the inhibition of different cyclic nucleotide phosphodiesterase isoforms by means of selective inhibitors and cGMP–elevating agents (Abstract Only), Mol. Pharmacol. 44(5) pp. 1027–1035 (1993).

Barnett, Mary S. et al., Initial biochemical and functional characterization of cyclic nucleotide phosphodiesterase isozymes in canine colonic smooth muscle (Abstract Only), J. Pharamcol. Exp. Ther., 264(2) pp. 801–812 (1993).

Molnar–Kimber, K. et al., Modulation of TNFa and IL–1B from indotoxin–stimulated monocytes by selective PDE isozyme inhibitors (Abstract Only), Agents Actions 39(Spec. Conf. Issue), C77–C79 (1993).

Giorgi, Mauro et al., Characterization of 3':5' cyclic nucleotide phosphodiesterase activities of mouse neuroblastoma N18TG2 cells (Abstract Only), FEBS Lett. 324(1) pp. 76–80 (1993).

Porter, Roderick et al., Preparation of 6–phenyl–3–(5–tetrazoly)pyridin–2(H)–one derivatives as cyclic AMP–dependent protein kinase agonists (Abstract Only), PCT Int. Appl. WO9206085 A1, (Sep. 26, 1991).

Molnar–Kimber, K. L. et al., Differential regulation of TNF–a and IL–1B production from endotoxin stimulated human monocytes by phosphodiesterase inhibitors (Abstract Only), Mediators Inflammation 1(6) pp. 411–417 (1992).

Radomski, Marek W. et al., Human Colorectal adenocarcinoma cells: differential nitric oxide synthesis determines their ability of aggregate platelets (Abstract Only), Cancer Res. 51(22) pp. 6073–6078 (1991).

Anderson, Thomas L. G. et al., Interactions between isoprenaline, sodium nitroprusside, and isozyme–selective phosphodiesterase inhibitors on ADP–induced aggretation and cyclic Nucleotide levels in human platelets (Abstract Only), J. Cardiovasc. Pharmacol. 18(2) pp. 237–242 (1991).

Souness, John E. et al., Role of Selective cyclic GMP phosphodiesterase inhibition in the myorelaxant actions of M&B 22,943, MY–5445, vinpocetine and 1–methyl–3–isobutyl–8–(methylamino)xanthine (Abstract Only), Br. J. Pharmacol. 98(3) pp. 725–734 (1989).

Lichtner, Rosemarie B., The pyrimidopyrimidine derivatives RA233 and RX–RA85 affect cell cycle distribution of two murine tumor cell lines (Abstract Only), Eur. J. Cancer Clin. Oncol. 25(6), pp. 945–951 (1989).

Mamytbekova, A., et al., Antimetastatic effect of flurbiprofen and other platelet aggregation inhibitors (Abstract Only), Neoplasma 33(4), pp. 417–421 (1986).

Hagiwara, Masatoshi et al., Effect of 1–(3–chloroanilino)–4–phenylpthalazine (MY–5445), a specific inhibitor of cyclic CMP phosphodiesterase, on human platelet aggregation (Abstract Only), J. Pharmacol. Exp. Ther. 229(2) pp. 467–471 (1984).

* cited by examiner

METHOD OF TREATING A PATIENT HAVING PRECANCEROUS LESIONS WITH PHENYL PURINONE DERIVATIVES

This application is a continuation of application Ser. No. 08/472,804, filed Jun. 7, 1995, now abandoned.

TECHNICAL FIELD

This invention relates to methods for treatment or prevention of precancerous lesions.

BACKGROUND OF THE INVENTION

Each year in the United States alone, untold numbers of people develop precancerous lesions. These lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds which prevent or induce the remission of existing precancerous or cancerous lesions or carcinomas would greatly reduce illness and death from cancer.

Approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation. Overall, about $2.5 billion is spent annually in the United States in colon cancer treatment and prevention.

As indicated above, each polyp carries with it a chance that it will develop into a cancer. The likelihood of cancer is diminished if a polyp is removed. However, many of these patients demonstrate a propensity for developing additional polyps in the future. They must, therefore, be monitored periodically for the rest of their lives for polyp reoccurrence.

In most cases (i.e. the cases of so-called common sporadic polyps), polyp removal will be effective to reduce the risk of cancer. In a small percentage of cases (i.e. the cases of the so-called polyposis syndromes), removal of all or part of the colon is indicated. The difference between common sporadic polyps and polyposis syndromes is dramatic. Common sporadic polyp cases are characterized by relatively few polyps, each of which can usually be removed leaving the colon intact. By contrast, polyposis syndrome cases can be characterized by many (e.g. hundreds or more) of polyps—literally covering the colon in some cases—making safe removal of the polyps impossible short of surgical removal of the colon.

Because each polyp carriers with it the palpable risk of cancerous development, polyposis syndrome patients invariably develop cancer if left untreated. Surgical removal of the colon is the conventional treatment. Many of these patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because therapy is often not effective and has severe side effects. Cancer prevention is important for recovered cancer patients who retain a risk of cancer reoccurrence. Also, cancer prevention is important for people who have not yet had cancer, but have hereditary factors that place them at risk of developing cancer. With the development of new diagnostic screening technologies, it is possible to identify those with high risk factors, such as the potential for polyposis syndrome, who would greatly benefit from chemopreventive drugs. Therefore, finding such anti-cancer drugs that can be used for prolonged preventive use is of vital interest to many people.

One way to find such drugs is to screen thousands of compounds for the same biological activity found in known chemopreventive and chemotherapeutic drugs. Most such drugs are now believed to kill cancer cells by inducing apoptosis, or as sometimes referred to as "programmed cell death." Apoptosis naturally occurs in virtually all tissues of the body, and especially in self-renewing tissues such as bone marrow, gut, and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis plays a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptosis effects, most chemotherapeutic drugs have serious side effects that prohibit their long term use, or use in otherwise healthy individuals with precancerous lesions. These side effects, which are a result of the high levels of cytotoxicity of the drugs, include hair loss, weight loss, vomiting and bone marrow immune suppression. Therefore, there is a need to identify new drug candidates for therapy that do not have such serious side effects in humans.

SUMMARY OF THE INVENTION

This invention is a method of treating patients with precancerous lesions or neoplasms by administering a pharmacologically effective amount of a compound of Formula I below to a patient in need of such treatment. Such compositions are effective in modulating apoptosis, and eliminating and inhibiting precancerous lesions, and neoplastic cells.

DETAILED DESCRIPTION OF THE PRESENTLY PREFERRED EMBODIMENTS

As discussed above, this invention is a method of treating a patient with precancerous lesions or neoplasms by administering a pharmacologically effective amount of the phenyl cycloamino pyrimidinone derivative represented by the following formula (I), or the pharmacologically acceptable salt thereof;

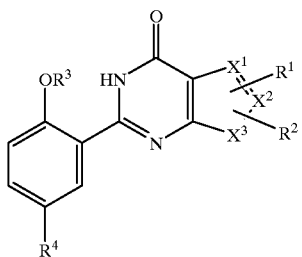

(I)

wherein $R^1$ is H; $C_1$–$C_3$ alkyl optionally substituted with one or more fluoro substituents; or $C_3$–$C_5$ cycloalkyl;

$R_2$ is H, or $C_1$–$C_6$ alkyl optionally substituted with one or more fluoro substituents or with $C_3$–$C_6$ cycloalkyl;

$R_3$ is $C_1$–$C_6$ alkyl optionally substituted with one or more fluoro substituents or with $C_3$–$C_6$ cycloalkyl; $C_3$–$C_5$ cycloalkyl; $C_3$–$C_6$ alkenyl; or $C_3$–$C_6$ alkynyl;

$R_4$ is $C_1$–$C_4$ alkyl optionally substituted with OH, $NR^5R^6$, CN, $CONR^5R^6$, $SO_2NR^5R^6$, or $CO_2R^7$; $C_2$–$C_4$ alkenyl optionally substituted with CN, $CONR^5R^6$ or $CO_2R^7$; $C_2$–$C_4$ alkanoyl optionally substituted with $NR^5R^6$; hydroxy $C_2$–$C_4$ alkyl optionally substituted with $NR^5R^6$; ($C_2$–$C_3$ alkoxy) $C_1$–$C_2$ alkyl optionally substituted with OH or $NR^5R^6$; $CONR^5R^6$; $CO_2R^7$; halo; $NR^5R^6$; $NHSO_2NR^5R^6$; $NHSO_2R^8$; or phenyl or heterocyclyl either of which is optionally substituted with methyl;

$R^5$ and $R^6$ are each independently H or $C_1$–$C_4$ alkyl, or together with the nitrogen atom to which they are attached form a pyrrolidinyl, piperidino, morpholino, 4-($NR^9$) piperazinyl or imidazolyl group wherein said group is optionally substituted with $C_1$–$C_4$ alkyl or hydroxy;

$R^7$ is H or $C_1$–$C_4$ alkyl;

$R^8$ is $C_1$–$C_3$ alkyl optioanlly substituted with $NR^5R^6$; and $R^9$ is H; $C_1$–$C_3$ alkyl optionally substituted with phenyl; hydroxy $C_2$–$C_3$ alkyl; or $C_1$–$C_4$ alkanoyl; and pharmaceutically acceptable salts thereof.

$X^1$, $X^2$ and $X^3$ may be independently nitrogen or carbon with the proviso that: at least two of $X^1$, $X^2$ and $X^3$ must be nitrogen.

"Alkyl group" refers to straight or branched chain $C_1$–$C_{12}$ groups such as methyl, ethyl, propyl, iso-propyl, n-butyl, t-butyl and amyl. "Alkoxy group" refers to hydroxy-substituted alkyl groups such as methoxy, ethoxy, propoxy, butoxy and amyloxy. "Alkoxycarbonyl group" refers to carbonyl-substituted alkoxy groups such as methoxycarbonyl, ethoxycarbonyl, propoxycarbonyl, butoxycarbonyl, amyloxycarbonyl, etc. "Alkylcarbonyl group" refers to carbonyl-substituted alkyl groups such as acetyl, propionyl, butyryl or others. "Halogen" refers to fluorine, chlorine, bromine and iodine. "Lower" refers to 6 or less carbon atoms. "Heterocyclyl" is selected from thienyl, pyridyl, pyrazolyl, imidazolyl, triazolyl, oxazolyl, thiazolyl or pyrimidinyl.

When $X_1$ and $X_2$ are nitrogen, a preferred group of compounds of formula (1) is that wherein $R^1$ is H, methyl or ethyl; $R^2$ is $C_1$–$C_3$ alkyl; $R^3$ is $C_2$–$C_3$ alkyl; $R^4$ is $C_1$–$C_2$ alkyl optionally substituted with OH, NR5R6, $CONR^5R^6$ or $CO_2R^7$; acetyl optionally substituted with $NR^5R^6$; hydroxyethyl substituted with $NR^5R^6$; ethoxymethyl optionally substituted with OH or $NR^5R^6$; CH=CHCN; CH=CHCONR$^5$R$^6$; CH=CHCO$_2$R$^7$; CO$_2$H; CONR$^5$R$^6$; BR; NR$^5$R$^6$; NHSO$_2$NR$^5$R$^6$; NHSO$_2$R$^8$; or pyridyl or imidazolyl either of which is optionally substituted with methyl $R^5$ and $R^6$ are each independently H, methyl or ethyl, or together with the nitrogen atom to which they are attached form a piperidino, morpholino, 4-($NR^9$)-1-piperazinyl or imidazolyl group wherein said group is optionally substituted with methyl or hydroxy; $R^7$ is H or t-butyl; $R^8$ is methyl or $CH_2CH_2CH_2NR^5R^6$; and $R^9$ is H, methyl, benzyl, 2-hydroxyethyl or acetyl.

Another preferred group of compounds is that wherein $R^2$ and $R^4$ are hydrogen; $R^3$ is lower alkyl and at least $X^1$ and $X^3$ are nitrogen.

The pharmacologically acceptable salt includes inorganic acid salts such as hydrochloride, hydrobromide, sulfate and phosphate; organic acid salts such as acetate, maleate, tartrate, methanesulfonate, benzenesulfonate and toluenesulfonate; and amino acid salts such as argininate, aspartate and glutamate. Further, some of the compounds may form metal salts such as Na, K, Ca or Mg, and the pharmacologically acceptable salt of formula (I) also includes these metal salts.

Although the compound of formula I may be present as various isomers including geometrical isomers, i.e., cis-isomer and trans-isomer. and optical isomers, i.e., d-isomer and l-isomer depending upon the kinds and combination of the substituents, it is needless to say that the compounds include all of the isomers.

As used herein, the term "precancerous lesion" refers to lesions that exhibit histologic changes which are associated with an increased risk of cancer development. Examples include adenomatous polyps of the colon, dysplastic nevi of the skin and atypical hyperplasia of the breasts. Certain syndromes that commonly display precancerous lesions are also referred to by the term "precancerous" including dysplastic nevus syndrome and the colonic polyposis syndromes. "Precancerous" refers to these lesions or syndromes of various tissues whether or not the lesions are clinically identifiable.

As used herein, the term "carcinomas" refers to lesions which are cancerous. Examples include malignant melanomas, breast cancer, and colon cancer.

As used herein, the term, "neoplasm" refers to both precancerous and cancerous lesions.

As used herein, the term "halo" or "halogen" refers to chloro, bromo, fluoro and iodo groups, and the term "alkyl" refers to straight, branched or cyclic alkyl groups.

Compounds of formula I may be formulated into compositions together with pharmaceutically acceptable carriers for injection, oral administration in solid or liquid form, or for rectal administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g. pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for rectal administration are preferably suppositories which may contain, in addition to the compounds of Formula I, excipients such as cocoa butter or a suppository wax.

The pharmaceutically acceptable carrier and compounds of Formula I are formulated into unit dosage forms for administration to a patient. The dosage levels of active ingredient (i.e. compounds of Formula I) in the unit dosage may be varied so as to obtain an amount of active ingredient effective to achieve polyp-eliminating activity in accordance with the desired method of administration (i.e. oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g. two to four times per day.

In another form, the invention is a method of inhibiting the growth of neoplastic cells by exposing them to an effective amount of the compound of Formula [I] above.

In still another form, the invention is a method of regulating apoptosis in human cells by exposing those cells to an effective amount of the compound of formula [I] above where such cells are sensitive to this compound.

Additionally, in yet another form, the invention is a method of treating a patient having a disease which would benefit from regulation of apoptosis by treating the patient with an effective amount of the compound of Formula [I] above. The regulation of apoptosis is believed to play an important role in diseases associated with abnormalities of cellular growth patterns such as benign prostatic hyperplasia, neurodegenerative diseases such as Parkinson's disease, autoimmune diseases including multiple sclerosis and rheumatoid arthritis, infectious diseases such as AIDS, and other diseases, as well.

The foregoing may be better understood from the following examples, which are presented for purposes of illustration and are not intended to limit the scope of the invention. As used in the following examples, the references to substituents such as R, $R^1$, $R^2$ etc., refer to the corresponding compounds and substituents in the Formula above.

Preferable specific examples of the compound will now be described in order to facilitate the understanding of the present invention, though it is needless to say that the compounds of the present invention are not limited to these examples.

EXAMPLE 1

2-(2-Propoxyphenyl)-6-purinone

A stirred mixture of 4,5-diamino-2-(propoxyphenyl) pyrimidin-6-one sulphate (1.5 g) (prepared by the addition of concentrated sulphuric acid to an ethanolic solution of the free base) and formamide (15 ml) was heated in an oil bath (temp. 190°–200° C.) for 70 minutes. When cool the mixture was filtered and the collected solid was washed with ethanol to give a crude product (1.1 g), m.p. 254°–259° C., which was recrystallised from ethanol to give the title compound, 0.72 g, m.p. 263°–265° C.

EXAMPLE 2

2-(2-Ethoxyphenyl)-6-purinone

In a similar manner to Example 1 reaction of 4,5-diamino-2-(2-ethoxyphenyl)pyrimidin-6-one sulphate (1.5 g) with formamide (15 ml) afforded the title compound, 0.36 g, m.p. 276°–277° C., (recrystallised from ethanol).

EXAMPLE 3

2-(2-Butoxyphenyl)-6-purinone

In a similar manner to Example 1 reaction of 4,5-diamino-2-(2-butoxyphenyl)pyrimidin-6-one sulphate (1.5 g) with formamide (5 ml) afforded the title compound, 0.65 g, m.p. 247°–248° C., (recrystallised from ethanol).

EXAMPLE 4

2-(2-Isobutoxyphenyl)-6-purinone

In a similar manner to Example 1 reaction of 4,5-diamino-2-(2-isobutoxyphenyl)pyrimidin-6-one sulphate (1.4 g) with formamide (5 ml) afforded the title compound, 0.24 g, m.p. 272°–273° C., (recrystallised from ethanol).

EXAMPLE 5

2-(2-Propoxyphenyl)purine-6,8-dione

A mixture of 4,5-diamino-2(2-propoxyphenyl)-pyrimidin-6-one (1.3 g), and urea (1.5 g) was heated in an oil bath (temp. 190° C.) for 45 minutes. The resultant solid was digested with hot water, the mixture filtered and the solid washed with water to give a crude product, 1.36 g. Recrystallisation from dimethylformamide gave the title compound (1.01 g), m.p. >350° C., $\delta$(DMSO-$d_6$), 1.01 (t, 3H); 1.88 (m, 2H); 4.09 (t, 2H); 7.10, 7.21, 7.52 and 7.76 (multiplets, 4H); ca 11.07, 11.55 and 11.95 (very broad singlets, 3H).

EXAMPLE 6

2-(2-Methoxyphenyl)purine-6,8-dione

In a similar manner to Example 5 reaction of 4,5-diamino-2-(2-methoxyphenyl)pyrimidin-6-one (0.93 g) with urea (1.20 g) afforded the title compound, 0.28 g, m.p. 329°–330° C. (recrystallised twice from dimethylformamide).

EXAMPLE 7

2-(2-Ethoxyphenyl)purine-6,8-dione

A solution of 4,5-diamino-2-(2-ethoxyphenyl)-pyrimidin-6-one sulphate (2.0 g) in water (50 ml) was neutralized with ammonium hydroxide and extracted with chloroform. The organic extract was evaporated under reduced pressure to dryness and the residual free base was treated in a similar manner to Example 5 with urea (1.74 g) to afford after recrystallisation from dimethyl-formamide the title compound, 0.66 g, m.p. 349°–351° C.

EXAMPLE 8

2-(2-Butoxyphenyl)purine-6,8-dione

In a similar manner to Example 5 reaction of 4,5-diamino-2-(2-butoxyphenyl)pyrimidin-6-one (0.96 g) with urea (1.05 g) afforded the title compound, 0.26 g, m.p. 324°–326° C., (recrystallised from dimethylformamide).

EXAMPLE 9

2-(2-Isobutoxyphenyl)purine-6,8-dione

Carbonyldiimidazole (1.01 g) was added to 4,5-diamino-2-(2-isobutoxyphenyl)pyrimidin-6-one (1.50 g) in toluene (100 ml) and the resulting mixture was heated under reflux for one hour yielding a brown solid which was collected. This solid was washed with water and recrystallised from dimethylformamide to yield the title compound, 0.22 g, m.p. >360° C.

EXAMPLE 10

2-(2-Allyloxyphenyl)purine-6,8-dione 4,5-Diamino-2-(2-allyloxyphenyl)pyrimidin-6-one sulphate (0.8 g) was added to a stirred solution of carbonyldiimidazole (0.72 g) in dry pyridine (8 ml) under nitrogen. The resulting solution was stirred under nitrogen for 3 hours at ambient temperature and then the volume of the solution was reduced by evaporation under reduced pressure. The residual syrup was diluted with aqueous acetone (50%, 20 ml) and the resultant solid was collected, washed with water and acetone and dried to give a crude product (0.48 g). This material together with another crude sample (0.1 g, prepared in a similar manner as hereinbefore described) was recrystallised from acetic acid (ca 25 ml) by the addition of hot water (5 ml) to afford, after washing with acetic acid, water and ethanol and drying, the title compound, 0.4 g, m.p. 340°–345° C. dec., δ (DMSO-$d_6$), 4.68 (m, 2H); 5.2–5.4 (m, 2H); 5.9–6.2 (m, 1H); 7.07–7.2, 7.4–7.55, 7.6–7.7 (m's, 4H); 10.9, 11.45 and 12.1 (broad singlets, 3H).

EXAMPLE 11

2-(2-Propoxyphenyl)-6-purinone

A mixture of 4,5-diamino-2-(2-propoxyphenyl)-pyrimidin-6-one (0.3 g), formamidine acetate (0.18 g) and anhydrous sodium acetate (0.1 g) was heated in an oil bath at 155°–165° C. for 2½ hours. The mixture melted and then resolidified. Ethanol (1 ml) was added and the title compound was collected by filtration, 0.31 g, m.p. 256°–258° C.

EXAMPLE 12

2-(2-Propoxyphenyl)purine-6,8-dione

In a similar manner to Example 9 reaction of carbonyldiimidazole (4.98 g) with 4,5-diamino-2-(2-propoxyphenyl) pyrimidin-6-one (7.00 g) in toluene (350 ml) afforded the title compound, 3.76 g, m.p. >340° C. (recrystallised from dimethylformamide).

EXAMPLE 13

6-(2-Ethoxyphenyl)-1-n-propyl-1,5-dihydro-4H-pyrazolo[3,4-d]pyrimidin-4-one

A solution of 5-(2-ethoxybenzamido)-1-n-propyl-pyrazole-4-carboxamide (Preparation 2; 0.541 g, 0.0017 mol) and sodium hydroxide (0.10 g, g, 0.0026 mol) in a mixture of water (5 ml) and ethanol 1 ml) was heated under reflux for 20 hours. The cool reaction solution was extracted with dichloromethane (5×30 ml), then the combined extracts dried ($Na_2SO_4$) and evaporated under vacuum to give the crude product. Purification by column chromatography ($SiO_2$, 5% MeOH in $CH_2Cl_2$) afforded the title compound as a white solid (0.45 g, 89%). Crystallisation of a sample from ethyl acetate-hexane gave colourless needles, m.p. 154–155° C. Found: C,64.45; H,5.97; N,18.89. $C_{16}H_{18}N_4O_2$ requires C,64.41; H,6.08; N,18.78%.

EXAMPLE 14

6-[2-Ethoxy-5-(4-methyl-1-piperazinylsulphonyl)phenyl]-1-n-propyl-1,5-dihydro-4H-pyrazolo[3,4-]pyrimidin-4-one A solution of N-methylpiperazine (0.79 g, 0.0079 mol) in ethanol (10 ml) was added to a stirred suspension of 6-(5-chlorosulphonyl-2-ethoxyphenyl)-1-propyl-1,5-dihydro-4H-pyrazolo[3,4-d]pyrimidin-4-one (Preparation 3; 0.78 g, 0.00197 mol) in ethanol (40 ml). After 2 hours at room temperature, the solvent was removed by evaporation under vacuum. The residue was partitioned between saturated aqueous sodium bicarbonate solution (20 ml) and dichloromethane (30 ml), the organic layer removed and the aqueous phase extracted with more dichloromethane (3×30 ml). The combined organic solutions were dried ($Na_2SO_4$) and the solvent removed by evaporation under vacuum. The residue was purified first by column chromatography ($SiO_2$, 5% MeOH in $CH_2Cl_2$) and then crystallisation from ethyl acetate to afford the title compound as white crystals (0.35 g, 35%), m.p. 82–84° C. Found: C,51.66; H,5.72; N,16.32. $C_{21}H_{28}N_6O_4S$; 9.5 $CH_2Cl_2$ requires C,51.39; H,5.72; N,16.72%.

EXAMPLE 15

6-[2-Ethoxy-5-(morpholinoacetyl)phenyl]-1-n-propyl-1,5-dihydro-4H-pyrazolo[3,4-d]-pyrimidin-4-one Morpholine (0.175 g, 0.002 mol) was added to a stirred suspension of 6-(5-bromoacetyl-2-ethoxyphenyl)-1-n-propyl-1,5-dihydro-4H-pyrazolo[3,4-d]pyrimidin-4-one (Preparation 4; 0.70 g, 0.0017 mol) and anhydrous potassium carbonate (0.461 g, 0.0033 mol) in acetonitrile (30 ml) and the resulting mixture stirred at room temperature for 3 hours. The solvent was removed by evaporation under vacuum, the residue partitioned between water (20 ml) and dichloromethane (30 ml), the organic phase removed and the aqueous phase extracted with dichloromethane (3×30 ml). The combined organic solutions were dried ($Na_2SO_4$) and the solvent removed by evaporation under vacuum to give a yellow oil. Purification by column chromatography ($SiO_2$, 5% MeOH in $CH_2Cl_2$), followed by crystallisation from ethyl acetate-hexane, provided the title compound as white crystals (0.62 g, 85%), m.p. 160–162° C. Found: C,61.96; H,6.29; N,16.32. $C_{22}H_{27}N_5O_4$ requires C,62.10; H,6.40; N,16.46%.

EXAMPLE 16

6-{2-Ethoxy-5-[4-(2-hydroxyethyl)-1-piperazinylacety]-phenyl}-1-n-propyl-1,5-dihydro-4H-pyrazolo[3,4-d]pyrimidin-4-one Prepared by the same method as Example 3 from N-(2-hydroxyethyl) piperazine (0.156 g, 0.0012 mol), 6-(5-bromoacetyl-2-ethoxyphenyl)-1-n-propyl-1, 5-dihydro-4H-pyrazolo[3, 4-d] pyrimidin-4-one (Preparation 4; 0.412 g, 0.001 mol) and anhydrous potassium carbonate (0.272 g, 0.002 mol) in acetonitrile (30 ml). The product was obtained as pale yellow crystals (0.34 g, 74%), m.p. 166–169° C., after crystallisation from ethyl acetate-hexane. Found: C,61.33; H,6.72; N,18.03. $C_{24}H_{32}N_6O_4$ requires C,61.52; H,6.88; N,17.94%.

EXAMPLE 17

6-[2-Ethoxy-5-(2,4-dimethyl-1-imidazolylacetyl)phenyl]-1-n-propyl-1,5-dihydro-4H-pyrazolo[3,4-d]pyrimidin-4-one Prepared by the same method as Example 3 from 2,4-dimethylimidazole hydrochloride (0.265 g, 0.002 mol), 6-(5-bromoacetyl-2-ethoxyphenyl)-1-n-propyl-1,5-dihydro-4H-pyrazolo[3,4-d]pyrimidin-4-one(0.412 g, 0.001 mol) and anhydrous potassium carbonate (0.272 g, 0.002 mol) in acetonitrile (30 ml). The product was obtained as a brown powder after crystallisation from ethyl acetate-hexane (0.10 g, 22%), m.p. 166° C. (dec.). Found C,60.82; H,5.69; N,17.93. $C_{23}H_{26}N_6O_3$; 0.3 $CH_2Cl_2$ requires C,60.84; H,5.82; N,18.27%.

EXAMPLE 18

6-(5-Bromo-2-ethoxyphenyl)-1-n-propyl-1,5-dihydro-4H-pyrazolo[3,4-d]pyrimidin-4-one A solution of N-bromosuccinimide (1.0 g, 0.0056 mol) in DMF (10 ml) was added dropwise to a stirred solution of 6-(2-ethoxyphenyl)-1-n-propyl-1,5-dihydro-4H-pyrazolo[3,4-d]pyrimidin-4-one (Example 1; 0.84 g, 0.0028 mol) in DMF (10 ml) and the resulting red solution stirred for 20 hours. The solvent was removed by evaporation under vacuum and the residue partitioned between saturated aqueous sodium bicarbonate solution (20 ml) and ethyl acetate (20 ml). The organic phase was removed and the aqueous phase extracted with ethyl acetate (3×30 ml). The combined organic solutions were dried and the solvent removed by evaporation under vacuum to give an orange crystalline solid. Recrystallisation from ethyl acetate-hexane gave the title compound as colourless crystals (0.812 g, 78%), m.p. 172–173° C. Found: C,51.13; H,4.41; N,14.84. $C_{16}H_{17}BrN_4O_2$ requires C,50.94; H,4.54; N,14.85%.

EXAMPLE 19

4-Ethoxy-3-(4-oxo-1-n-propyl-1,5-dihydro-4H-pyrazolo-[3,4-d]pyrimidin-6-yl)benzoic acid n-Butyllithium (2.5 M solution in hexane, 2.0 ml, 0.005 mol) was added dropwise to a stirred solution of 6-(5-bromo-2-ethoxyphenyl)-1-n-propyl-1,5-dihydro-4H-pyrazolo[3, 4-d]pyrimidin-4-one (0.755 g, 0.002 mol) in dry THF (20 ml) at −78° C. under a dry nitrogen atmosphere. The bright yellow solution was stirred for 1 hour at −78° C., then excess crushed solid carbon dioxide was added and the resulting solution was allowed to warm to room temperature. Saturated aqueous ammonium chloride solution (3 ml) was then added and the solvents removed by evaporation under vacuum. The residue was partitioned between saturated aqueous sodium carbonate solution (30 ml) and dichloromethane (30 ml), the organic phase was removed and the aqueous phase extracted with further dichloromethane (3×30 ml). The aqueous phase was then acidified to pH 1 with concentrated hydrochloric acid and extracted with ethyl acetate (5×40 ml). The combined ethyl acetate extracts were dried ($Na_2SO_4$) and the solvent removed by evaporation under vacuum to give a white solid. Crystallisation from ethyl acetate-methanol gave the title compound as a white powder (0.130 g, 19%), m.p. 277–279° C. Found: C,59.64; H,5.19; N,16.39. $C_{17}H_{18}N_4O_4$ requires C,59.64; H,5.23; N,16.37%.

EXAMPLE 20

6-[2-Ethoxy-5-(4-methyl-1-piperazinylcarbonyl)phenyl]-1-n-propyl-1,5-dihydro-4H-pyrazolo[3,4-d]pyrimidin-4-one Excess oxalyl chloride (3 ml) was added dropwise to a stirred suspension of 4-ethoxy-3-(4-oxo-1-n-propyl-1,5-dihydro-4H-pyrazolo[3,4-d]pyrimidin-6-yl)benzoic acid (Example 7; 0.040 g, 0.0001 mol) in a mixture of DMF (1 drop) and dichloromethane (10 ml). After 2 hours at room temperature, the solvent was removed by evaporation under vacuum and the residue dissolved in dichloromethane (10 ml). Excess N-methylpiperazine (0.1 ml) was then added and the resulting mixture stirred for 15 minutes before being evaporated to dryness under vacuum. The residue was dissolved in saturated aqueous sodium bicarbonate solution (10 ml) and the solution extracted with ethyl acetate (6×30 ml). The combined extracts were dried ($Na_2SO_4$) and the solvent removed by evaporation under vacuum. The resulting solid was purified by column chromatography ($SiO_2$, 5% MeOH in $CH_2Cl_2$) to give the title compound as a white powder (0.028 g, 56%), m.p. 124–127° C. Found: C,62.06; H,6.26; N,19.44. $C_{22}H_{28}N_6O_3$ requires C,62.25; H,6.65; N,19.80%.

EXAMPLE 21

3-Methyl-6-(2-n-propoxyphenyl)-1-n-propyl-1,5-dihydro-4H-pyrazolo[3,4-d]-pyrimidin-4-one The title compound was prepared from 3-methyl-5-(2-n-propoxybenzamido)-1-n-propylpyrazole-4-carboxamide (Preparation 7; 5.456 g, 0.0016 mol) and sodium hydroxide (3.16 g, 0.079 mol) in a mixture of water (150 ml) and ethanol (30 ml), by the method of Example 13, and was obtained as a white solid (4.863 g, 94%) after column chromatography. A sample crystallised from ethyl acetate-hexane as colourless needles, m.p. 112–114° C. Found: C,66.35; H,6.79; N,17.12. $C_{18}H_{22}N_4O_2$ requires C,66.24; H,6.79; N,17.17%.

EXAMPLE 22

3-Methyl-6-[5-(morpholinosulphonyl)-2-n-propoxyphenyl]-1-n-propyl-1,5-dihydro-4H-pyrazolo[3,4-d]-pyrimidin-4-one The title compound was prepared from morpholine (0.451 g, 0.0052 mol) and 6-(5-chlorosulphonyl-2-n-propoxyphenyl)-3-methyl-1-n-propyl-1,5-dihydro-4H-pyrazolo[3,4-d]pyrimidin-4-one (Preparation 8; 0.55 g, 0.0013 mol), according to the procedure of Example 14, and was obtained as colourless needles (0.403 g, 65%), m.p. 161–163° C., after crystallisation from ethyl acetate-hexane.

Found: C,55.68; H,6.16; N,14.85. $C_{22}H_{29}N_5O_5S$ requires C,55.56; H,6.15; N,14.73%.

EXAMPLE 23

6-(5-Bromo-2-n-propoxyphenyl)-3-methyl-1-n-propyl-1, 5-dihydro-4H-pyrazolo[3,4-d]pyrimidin-4-one The title compound was prepared from N-bromosuccinimide (4.9 g, 0.0276 mol) and 3-methyl-6-(2-n-propoxyphenyl)-1-n-propyl-1,5-dihydro-4H-pyrazolo-[3,4-d]pyrimidin-4-one (Example 18; 3.0 g, 0.0092 mol), following the procedure of Example 6, and was obtained as yellow crystals (1.11 g, 30%), m.p. 157–159° C., after crystallisation from ethyl acetate. Found: C,53.14; H,5.17; N,13.76. $C_{18}H_{21}BrN_4O_2$ requires C,53.34; H,5.22; N,13.82%.

EXAMPLE 24

(E)-3-(3-Methyl-4-oxo-1-n-propyl-1,5-dihydro-4H-pyrazolo [3,4-d]pyrimidin-6-yl)-4-n-propoxycinnamic acid t-butyl ester To a solution of 6-(5-bromo-2-n-propoxyphenyl)-3-methyl-1-n-propyl-1,5-dihydro-4H-pyrazolo[3,4-d] pyrimidin-4-one (Example 11; 2.14 g, 0.0053 mol) and triethylamine (0.81 g, 0.008 mol) in acetonitrile (4 ml), was added palladium(II) acetate (0.06 g, 0.00027 mol), tri-o-tolylphosphine (0.16 g, 0.00053 mol) and t-butyl acrylate (1.03 g, 0.008 mol). The mixture was heated under reflux for 4 hours, cooled to room temperature and then partitioned between water (30 ml) and dichloromethane (30 ml). The organic phase was removed and the aqueous phase extracted with dichloromethane (2×30 ml). The combined organic solutions were dried ($Na_2SO_4$) and the solvent removed by evaporation under vacuum to give a greenish brown solid. Purification by column chromatography ($SiO_2$, $CH_2Cl_2$ then 2% MeOH in $CH_2Cl_2$) and crystallisation from ethyl acetate-hexane afforded the title compound as white crystals (1.48 g, 58%), m.p. 181–182° C. Found: C, 66.50; H, 6.75; N, 12.27. $C_{25}H_{32}N_4O_4$ requires C, 66.35; H, 7.12; N, 12.38%.

EXAMPLE 25

(E)-3-(3-Methyl-4-oxo-1-n-propyl-1,5-dihydro-4H-pyrazolo[3,4-d]pyrimidin-6-yl)-4-n-propoxycinnamic acid 2N Aqueous sodium hydroxide solution (8.0 ml, 0.016 mol) was added to a solution of (E)-3-(3-methyl-4-oxo-1-n-propyl-1,5-dihydro-4H-pyrazolo[3,4-d]pyrimidin-6-yl)-4-n-propoxycinnamic acid t-butyl ester (Example 12; 1.8 g, 0.004 mol) in methanol (8 ml) and the mixture heated under reflux for 5 hours. The methanol was removed by evaporation under vacuum and the aqueous solution acidified to pH 1 with 2N hydrochloric acid. Exhaustive extraction of the product with 10% methanol in ethyl acetate was followed by drying of the combined extracts ($Na_2SO_4$) and evaporation of solvents under vacuum to furnish an off-white solid. Crystallisation from ethyl acetate-methanol afforded the title compound as white crystals (0.18 g, 12%), m.p. 231–232° C. Found: C, 63.52; H, 5.96; N, 14.00. $C_{21}H_{24}N_4O_4$ requires C, 63.62; H, 6.10; N, 14.13%.

EXAMPLE 26

N-[(E)-3-(3-Methyl-4-oxo-1-n-propyl-1,5-dihydro-4H-pyrazolo[3,4-d]pyrimidin-6-yl)-4-n-propoxy-cinnamoyl]morpholine To a stirred solution of (E)-3-(3-methyl-4-oxo-1-n-propyl-1,5-dihydro-4H-pyrazolo[3,4-d]pyrimidin-6-yl)-4-n-propoxycinnamic acid (Example 13; 1.0 g, 0.0025 mol) and morpholine (0.21 g, 0.0025 mol) in dichloromethane at 0° C. was added, sequentially, N-methylmorpholine (0.5 g, 0.005 mol), 1-hydroxybenzotriazole hydrate (0.383 g, 0.0025 mol) and 1-(3-dimethylaminopropyl)-3-ethylcarbodiimide hydrochloride (0.957 g, 0.005 mol). The reaction mixture was allowed to warm to room temperature, stirred for 20 hours and evaporated under vacuum, then the residue partitioned between water (30 ml) and dichloromethane (30 ml). The organic phase was removed and the aqueous phase extracted with more dichloromethane (2×30 ml); the combined organic solutions were then dried ($Na_2SO_4$ and the solvent removed under vacuum to give a white solid. Purification by column chromatography ($SiO_2$, $CH_2Cl_2$ then 3% MeOH in $CH_2Cl_2$) and crystallisation from ethyl acetate-hexane-methanol afforded the title compound as white crystals (0.74 g, 63%), m.p. 156–157° C. Found: C, 64.60; H, 6.85; N, 15.16. $C_{25}H_{31}N_5O_4$ requires C, 64.50; H,, 6.71; N, 15.04%.

EXAMPLE 27

N-{3-[3-(3-Methyl-4-oxo-1-n-propyl-1,5-dihydro-4H-pyrazolo[3,4-d]pyrimidin-6-yl)-4-n-propoxyphenyl]-propanoyl}morpholine A solution of N-[(E)-3-(3-methyl-4-oxo-1-n-propyl-1,5-dihydro-4H-pyrazolo[3,4-d]pyrimidin-6-yl)-4-n-propoxycinnamoyl]morpholine (0.5 g, 0.0011 mol) in ethanol (30 ml) was stirred with 10% palladium on charcoal catalyst (0.05 g) under a hydrogen pressure of 50 p.s.i. (3.45 bar) at room temperature for 14 hours. The reaction mixture was filtered and solvent removed by evaporation under vacuum. Trituration of the residue with diethyl ether, followed by crystallisation from ethyl acetate-hexane, afforded the title compound as white crystals (0.37 g, 74%), m.p. 132–133° C. Found: C, 64.39; H, 7.26; N, 14.80. $C_{25}H_{33}N_5O_4$ requires C, 64.22; H, 7.11; N, 14.98%.

EXAMPLE 28

6-(2-Propoxyphenyl)pyrazolo[3,4-d]pyrimidin-4(5H)-one

A stirred mixture of 2-propoxybenzamidine methanesulphonate (1.0 g), 3-amino-4-pyrazole-carboxamide sulphate (0.5 g) and sodium acetate (0.82 g) was heated in an oil bath (180° C.) for one hour. The reaction mixture was dissolved in hot 2 Normal sodium hydroxide (10 ml) and the solution was treated with charcoal and neutralised with glacial acetic acid. A precipitate was collected, washed with water and eluted from a silica column with chloroform. The combined fractions containing product were evaporated to dryness to afford the title compound, 148 mg, m.p. 182–183.5° C.

EXAMPLE 29

2-(2-Propoxyphenyl)thieno[2,3-d]pyrimidin-4(3H)-one a) A solution of 2-propoxybenzoyl chloride (0.99 g) in acetonitrile (7.5 ml) was added dropwise over 5 minutes to a cooled (0° C.), stirred mixture of 2-aminothiophene-3-carboxamide (0.71 g) and triethylamine (0.51 g) in acetonitrile (7.5 ml). The reaction mixture was stirred for one hour while being allowed to warm to ambient temperature and was then allowed to stand overnight. Acetonitrile was removed under reduced pressure and the residue was washed with water and recrystallised from ethanol-water to afford 2-(2-propoxybenzamido)thiophene-3-carboxamide, 0.91 g, m.p. 176.5–178.5° C.

b) A stirred mixture of 2-(2-propoxybenzamido)thiophene-3-carboxamide (0.90 g) and pyridine (1 ml) in 2

Normal sodium hydroxide (25 ml) was heated under reflux for hours. The cooled reaction mixture was neutralised with concentrated hydrochloric acid to afford a precipitate and the resulting mixture was extracted with chloroform (3×25 ml). The combined extracts were washed with water (20 ml) and brine (20 ml), dried magnesium sulphate) and evaporated under reduced pressure to afford a crude product which was recrystallised from ethanol-water to afford the title compound, 0.41 g, m.p. 115–117° C.

EXAMPLE 30

2-(2-Propoxyphenyl) [1,2,5]oxadiazolo[3,4-d]pyrimidin 4(3H)-one

Lead tetraacetate (1 g) was added portionwise over 5 minutes to a stirred solution of 4-amino-5-nitroso-2-(2-propoxyphenyl)pyrimidin-6-one (0.52 g) in acetic acid (10 ml) under nitrogen. The reaction mixture was stirred for 1.5 hours and then allowed to stand overnight. A precipitate was collected, washed with water, dissolved in hot methanol and treated with charcoal. The methanolic solution was filtered through diatomaceous earth and the filtrate was evaporated under reduced pressure to afford a residue which was recrystallised from methanol to afford the title compound, 0.19 g, m.p. 163–164° C.

EXAMPLE 31

2-(2-Propoxyphenyl) [1,2,5]thiadiazolo[3,4-d]pyrimidin-4(3H)-one

A stirred solution of 4,5-diamino-2-(2-propoxyphenyl) pyrimidin-6-one sulphate (0.72 g) in thionyl chloride (25 ml) was heated under reflux for 2 hours. The cooled reaction mixture was evaporated under reduced pressure and the residue was washed with water and recrystallised from methanol-water and then from methanol to afford the title compound, 0.38 g, m.p. 157.5–158.5° C.

EXAMPLE 32

2-(2-[2,2,2-Trifluoroethoxy]phenyl)purin-6-one a) A solution of 2-(2,2,2-trifluoromethoxy)benzamide (17 g, known from U.S. Pat. No. 3,766,247) and triethyloxonium tetrafluoroborate (about 28 g) in dichloromethane (140 ml) was allowed to stand for 20 hours. The solution was washed with saturated sodium carbonate solution, brine, dried over magnesium sulphate and evaporated to low volume under reduced pressure. The addition of ether (100 ml) and concentrated hydrochloric acid (6.5 ml) gave a solid which was recrystallised from ethanol-ether to give ethyl 2-(2,2,2-trifluoromethoxy)benzimidate hydrochloride, 12.88 g, m.p. 142.5–144° C. (after transition 119–121° C.).

b) A solution of the above benzimidate hydrochloride (12.6 g) in saturated methanolic ammonia (75 ml) was allowed to stand for 40 hours. Evaporation to low volume gave a slurry which was diluted with ether to give 2-(2,2, 2-trifluoromethoxy)benzamidine hydrochloride, 10.84 g, m.p. 248–251° C. Recrystallisation from ethanol-ether gave an analytical sample m.p. 250–252° C.

c) A stirred mixture of the above benzamidine hydrochloride (10 g) and ethyl cyanoglyoxylate oxime (7.2 g) in sodium ethoxide solution (from sodium, 3.6 g, and ethanol, 300 ml) was heated under reflux for 5 hours. The mixture was evaporated under reduced pressure to a quarter volume, diluted with cold water (400 ml) and 2 Normal hydrochloric acid was added to pH 6. Filtration gave 4-amino-5-nitroso-2-(2-[2,2,2-trifluoroethoxy]phenyl)pyrimidin-6-one, 5.79 g, m.p. 210–212° C., which was used directly in the next stage.

d) Sodium dithionite (3.88 g) was added during 5 minutes to a stirred partial solution of the above nitroso compound (3.5 g) and sodium bicarbonate (0.95 g) in 50% aqueous acetonitrile (180 ml) at 65° C. The resultant solution was stirred at 70° C. for a further 10 minutes and then the bulk of the acetonitrile was removed by evaporation under reduced pressure. The cold mixture was filtered to give crude 4,5-diamino-2-(2-[2,2,2-trifluoroethoxy)phenyl)-pyrimidin-6-one, which was dissolved in the minimum volume of hot ethanol and converted into the sulphate salt (2.33 g, m.p. 255–260° C. dec) by the addition of sulphuric acid. Recrystallisation from 50% aqueous ethanol gave the hemisulphate as a partial hydrate, m.p. ca. 210–220° C. dec.

e) A stirred mixture of the above diamine hemisulphate (1.1 g) and formamide (1 ml) was heated in an oil bath (temperature 195° C.) for 2 hours. The solution was cooled and diluted with water (44 ml) to give 0.92 g of a solid m.p. 261–263° C. Recrystallisation from ethanol gave the pure title compound, 0.77 g, m.p. 276–277° C. (transition 263° C.).

EXAMPLE 33

2-(2-Cyclopropylmethoxyphenyl)purin-6-one

A stirred mixture of 4,5-diamino-2-(2-cyclopropylmethoxyphenyl)pyrimidin-6-one sulphate (1.48 g) and formamide (5 ml) was heated in an oil bath at 180° C. for 2 to 3 hours. The cooled mixture was filtered and the collected solid was washed with ethanol to give a crude product (1.07 g) which was recrystallised three times from ethanol to afford the title compound, 0.32 g, m.p. 259–260° C.

EXAMPLE 34

2-(2–Cyclopropylmethoxyphenyl)purin-6,8-dione

A mixture of 4,5-diamino-2-(2-cyclopropylmethoxyphenyl)pyrimidin-6-one (0.90 g) and urea (0.99 g) was heated in an oil bath at 160° to 170° C. for one hour. The resultant solid was digested with warm water and the mixture filtered to afford a solid (0.74 g) which was twice recrystallised from dimethylformamide to afford a crude product (0.34 g). This together with another sample (0.22 g) similarly prepared from 4,5-diamino-2-(2-cyclopropylmethoxyphenyl)pyrimidin-6-one (0.45 g) was twice recrystallised from dimethylformamide to afford the title compound, 0.34 g, m.p. 329–331° C.

EXAMPLE 35

2-(2-Benzyloxyphenyl)purin-6,8-dione 2-(2-Benzyloxyphenyl)-4-amino-5-nitrosopyrimidine-6-one (2.0 g) was suspended in 50 ml of 1:1 acetonitrile : water and heated to 70° C. A solution of sodium dithionite (1.9 g) in water (10 ml) was added dropwise over 5 minutes and heating continued for a further 10 minutes. The solution was cooled to room temperature, poured into saturated aqueous sodium hydrogen carbonate (250 ml) and extracted with dichloromethane. The organic extract was dried (magnesium sulphate), concentrated to about 50 ml and treated with carbonyl diimidazole (1.3 g). After 16 hours, solvents were removed in vacuo and the residue recrystallised from dimethylformamide/water to afford the title compound, 1.2 g, m.p. 295° C. (dec).

EXAMPLE 36

2-(2-propoxyphenyl)-8-trifluoromethylpurin-6-one a) 4.5-Diamino-2-(2-propoxyphenyl)pyrimidin-6-one sulphate (1 g) and trifluoroacetic anhydride (10 ml) were heated together under reflux for 2 hours. Potassium carbonate (0.38 g) was added and the mixture was heated for a further 2 hours. The residue left after evaporation was treated with water (25 ml) and potassium carbonate was added to pH 5 to give 0.92 g of solid m.p. 192–199° C. Purification by column chromatography (silica gel, chloroform) gave 0.88 g of a solid m.p. 198–201° C., which was recrystallised from isopropyl acetate and then acetonitrile to give an analytical sample of 5-trifluoroacetylamino-4-amino-2-(2-propoxyphenyl)pyrimidin-6-one, m.p. 203–204° C.

b) A melt of the above trifluoroacetylamino derivative (0.62 g) was heated under nitrogen in an oil bath (temperature 250° C.) for 10 minutes to give a solid, m.p. 255–260° C. Recrystallisation from ethanol gave the pure title compound, 0.3 g, m.p. 267–269° C.

EXAMPLE 37

2-(2-Propoxyphenyl)-8-phenylpurin-6-one

A mixture of 4,5-diamino-2-(2-propoxyphenyl)-pyrimidine-6-one (1.3 g), benzamidine hydrochloride (2 g) and anhydrous sodium acetate (0.9 g) was heated in an oil bath (temperature 160–170° C.) for 2 hours. The reaction mixture was digested with hot ethanol to give a solid, 0.76 g, m.p. 267–271° C. This was combined with a further sample, 0.2 g, (similarly prepared) and recrystallised from aqueous acetic acid to give the title compound, 0.74 g, m.p. 259–260° C.

EXAMPLE 38

2-(2-Propoxyphenyl)-8-methylpurin-6-one

A mixture of 4,5-diamino-2-(2-propoxyphenyl) pyrimidin-6-one (1.56 g), anhydrous sodium acetate (1.14 g) and acetamidine hydrochloride (1.42 g) was heated in an oil bath at 150–160° C. for 2 hours. The mixture was digested with ethanol (2 ml), cooled, filtered and the solid washed with ethanol. Recrystallisation from ethanol gave the title compound, 0.72 g, m.p. 264–265° C.

EXAMPLE 39

2-(2-Propoxyphenyl)-8-mercaptopurin-6-one

A mixture of 4,5-diamino-2-(2-propoxyphenyl) pyrimidin-6-one (1.3 g), anhydrous potassium acetate (0.34 g) and thiourea (0.96 g) was heated at 170–180° C. for 2 hours. After digestion with water the mixture was filtered and the solid was dissolved in 1 Normal sodium hydroxide solution then re-precipitated by the addition of acetic acid. The dried solid was digested with chloroform and with ethanol to leave 1.12 g of a crude product. Repeated recrystallisations from dimethylformamide, 2-methoxyethanol, and acetic acid yielded the title compound, 0.32 g, m.p. 305–307° C.

EXAMPLE 40

2-(2-Propoxyphenyl)-8-methylthiopurin-6-one

Methyl iodide (0.5 g) was added to a stirred solution of 2-(2-propoxyphenyl)-8-mercaptopurin-6-one (1.0 g) in 1 Normal sodium hydroxide solution (8 ml). After 2.5 hours at room temperature the solution was neutralised with dilute hydrochloric acid to give the crude product which was recrystallised three times from aqueous ethanol to give the title compound, 0.32 g, m.p. 245–247° C.

EXAMPLE 41

2-(2-Propoxyphenyl)-8-aminopurin-6-one

A partial solution of 4,5-diamino-2-(2-propoxyphenyl) pyrimidin-6-one sulphate (1.1 g), cyanogen bromide (0.33 g), and sodium acetate trihydrate (0.42 g) in 50% aqueous ethanol (44 ml) was stirred at room temperature for 2 hours then allowed to stand overnight. The stirred mixture was then heated in a water bath (temperature 65° C.) for 3 hours, extra cyanogen bromide (0.05 g) added, and the mixture heated for a further 2 hours. The suspension was subjected to partial evaporation under reduced pressure then ammonium hydroxide was added to pH 5. The crude product was collected by filtration and recrystallised from acetonitrile to give the pure title compound, 0.6 g, m.p. 322–335° C. dec. (after melting about 200° C.). NMR (DMSO-$d_6$; 250 MHz) δ: 0.9 (3H, t) ; 1.6 (2H, m) ; 3.9 (2H, t); 6.8 (2H, s); 6.8 (2H, s); 6.9–7.1 (2H, m); 7.3–7.5 (3H, m).

EXAMPLE 42

2-(2-Propoxy-5-nitrophenyl)purin-6-one

A mixture of fuming nitric acid (0.23 ml) and sulphuric acid (4 ml) was added dropwise to a stirred solution of 2-(2-propoxyphenyl)purin-6-one (1.0 g) in sulphuric acid (4 ml) at 0 to -5° C. The temperature was maintained between –5° C. and +4° C. for 20 hours and then the mixture was poured into ice-water. The filtered solution was treated with concentrated ammonium hydroxide to pH 9 to give a crude product, 0.55 g. Recrystallisation twice from aqueous ethanol then once from acetonitrile gave the title compound, 0.2 g, m.p. 254–256° C.

EXAMPLE 43

2-(2-Propoxy-5-acetamidophenyl)purin-6-one

A solution of the crude product of Example 42 (1.5 g) in water (50 ml) containing 2 Normal sodium hydroxide (2.3 ml) and 10% palladium on charcoal (0.15 g) was shaken under hydrogen (50 psi) until the uptake was complete. Neutralisation of the filtered solution with acetic acid gave a fine precipitate of 2-(5-amino-2-propoxyphenyl)-purin-6-one. This mixture was warmed with 2 Normal hydrochloric acid (2.5 ml) and the solution was treated with acetic anhydride (0.55 ml) and sodium acetate trihydrate (0.8 g). The mixture was warmed for 10 minutes then cooled and filtered to give a crude product (1.02 g) which was recrystallised from aqueous dimethylformamide twice to give the title compound, 0.49 g, m.p. 320–323° C.

EXAMPLE 44

2-(2-propoxy-4-methoxyphenyl)purin-6-one a) A stirred mixture of methyl 4-methoxysalicylate (25 g), bromopropane (15.6 ml), potassium iodide (2.82 g) and anhydrous potassium carbonate (27.53 g) was heated under reflux for 48 hours. The cooled reaction mixture was filtered and the filtrate was evaporated under reduced pressure to yield an oil which was dissolved in diethyl ether (200 ml). The ethereal solution was extracted with aqueous sodium hydroxide to remove unreacted starting material and the organic phase was then washed with water and brine, dried (magnesium sulphate) and evaporated under reduced pressure to yield methyl4-methoxy-2-propoxy-benzoate, 22.45 g.

b) Methyl 4-methoxy-2-propoxybenzoate, (22.35 g) was treated with a saturated solution of ammonia in dry methanol (150 ml) for 6 hours at 80° C. in a pressure vessel. From the cooled reaction mixture was collected as a precipitate a crude sample of 4-methoxy-2-propoxybenzamide, 8.9 g. Recrystallisation from acetonitrile gave an analytical sample, m.p. 130–132° C.

c) A mixture of 4-methoxy-2-propoxybenzamide (15 g) and triethyloxonium tetrafluoroborate (0.08 mol) in dichloromethane (180 ml) was stirred at ambient temperature for about 60 hours. The reaction mixture was evaporated under reduced pressure and the residue was washed with diethyl either to yield crude ethyl 4-methoxy-2-propoxybenzimidate tetrafluoroborate, 20.52 g which was used without further purification.

d) A mixture of the above imidate salt (20.40 g) and saturated ethanolic ammonia (150 ml) was stirred for 18 hours at ambient temperature. Excess ammonia was removed by evaporation on a steam bath and the reaction mixture was evaporated under reduced pressure to low volume (50 ml). Concentrated hydrochloric acid (8 ml) was added and the mixture was evaporated under reduced pressure to yield a residue which was triturated with diethyl ether and a little ethanol to yield 4-methoxy-2-propoxybenzamidine hydrochloride, 7.67 g.

e) A stirred mixture of the above benzamidine hydrochloride (7.63 g) and ethyl cyanoglyoxylate-2-oxime (4.43 g) in sodium ethoxide solution (from sodium, 2.85 g, and ethanol, 120 ml) was heated under reflux for 3.5 hours. The cooled reaction mixture was evaporated to dryness and the residue was dissolved in water. Addition of hydrochloric acid yielded a precipitate which was collected, washed with water, digested with warm ethanol and finally washed with ethanol and diethyl ether to yield a solid (2.50 g). This was stirred in dilute hydrochloric acid for 10 minutes, filtered and washed with water to yield 2-(4-methoxy-2-propoxyphenyl)-4-amino-5-nitroso-pyrimidin-6-one, 2.16 g, m.p. 242–245° C. (dec).

f) A stirred mixture of the above nitroso compound (2.10 g), sodium bicarbonate (1.28 g) and sodium dithionite (2.64 g) in 50% aqueous acetonitrile (150 ml) was heated at 70° C. for 10 minutes and then chilled for 30 minutes. A two phase system formed. The upper organic phase was separated, washed with brine and reduced in volume to about 5 ml. This was dissolved in ethanol (20 ml), treated with concentrated sulphuric acid (1 ml) and concentrated by evaporation until precipitation began to occur. The cooled mixture yielded 2-(4-methoxy-2-propoxyphenyl)-4,5-diaminopyrimidin- 6-one sulphate, 1.06 g, m.p. 209–212° C. (dec). The aqueous phase was concentrated to about half volume and was extracted with chloroform (3×25 ml). The combined organic extracts were washed with water and brine, dried (magnesium sulphate) and evaporated to dryness. The residue was dissolved in ethanol (15 ml) and treated with concentrated sulphuric acid (0.5 ml) and the resulting solution was evaporated until precipitation occurred. A little diethyl ether was added and the cooled mixture afforded a further sample of the above diamine sulphate, 0.26 g, m.p. 213–6° C. (dec).

g) A stirred mixture of the above diamine sulphate (0.75 g) and formic acid (5 ml) was heated under reflux for 4.5 hours. The cooled reaction mixture was poured into water (25 ml) and the resultant mixture was centrifuged for 15 minutes to yield a solid (0.60 g) which together with another sample (0.25 g), similarly prepared, was recrystallised from 50% aqueous ethanol to afford the title compound, 0.60 g, m.p. 290–1° C. (dec).

EXAMPLE 45

2-(2-Propoxy-5-methoxyphenyl)purin-6-one

In a similar manner to Example 44:

a) reaction of 5-methoxy-2-propoxybenzamide (10.88 g) with triethyloxonium tetrafluoroborate (0.07 mol) yielded ethyl 5-methoxy-2-propoxybenzimidate tetrafluoroborate (21.0 g);

b) reaction of the above imidate salt (16.92 g) with a saturated solution of ethanolic ammonia (150 ml) yielded crude 5-methoxy-2-propoxybenzamidine (9.98 g);

c) reaction of the above amidine (9.98 g) with ethyl cyanoglyoxylate-2-oxime (6.86 g) and sodium ethoxide (from sodium, 3.31 g, and ethanol, 100 ml) yielded 2-(5-methoxy-2-propoxyphenyl)-4-amino-5-nitrosopyrimidin-6-one (6.63 g);

d) reaction of the above nitroso compound (3.80 g) with sodium dithionite (4.83 g) and sodium bicarbonate (2.33 g) yielded on treatment with concentrated sulphuric acid 2-(5-methoxy-2-propoxyphenyl)-4,5-diaminopyrimidin-6-one sulphate, 2.49 g, m.p. 221–224° C. (dec);

e) reaction of the above diamine sulphate (1.80 g) with formic acid (10 ml) yielded the title compound, 0.61 g, m.p. 233–4° C. (recrystallised from 25% aqueous ethanol).

EXAMPLE 46

2-(2-Propoxy-5-chlorophenyl)purin-6-one

In a similar manner to Example 44:

a) reaction of 5-chloro-2-propoxybenzamide (16.50 g) with triethyloxonium tetrafluoroborate (0.096 mol) yielded crude ethyl 5-chloro-2-propoxybenzimidate tetrafluoroborate (29.14 g);

b) reaction of the above imidate salt (29.14 g) with a saturated solution of ethanolic ammonia (200 ml) yielded 5-chloro-2-propoxybenzamidine (9.30 g);

c) reaction of the above amidine (4.50 g) with ethyl cyanoglyoxylate-2-oxime (4.43 g) and sodium ethoxide (from sodium, 1.46 g, and ethanol, 100 ml) yielded 2-(5-chloro-2-propoxyphenyl)-4-amino-5-nitrosopyrimidin-6-one (1.89 g);

d) reaction of the above nitroso compound (1.02 g) with sodium dithionite (1.26 g) and sodium bicarbonate (0.61 g) yielded on treatment with concentrated sulphuric acid 2-(5-chloro-2-propoxyphenyl)-4, 5-diaminopyrimidin-6-one sulphate, 0.81 g, m.p. 220–223° C.;

e) reaction of the above diamine sulphate (0.60 g) with formic acid (3 ml) yielded the crude title compound, (0.48 g) which together with another sample (0.48 g), similarly prepared, was recrystallised from 50% aqueous ethanol to afford the title compound, 0.61 g, m.p. 277–9° C.

The starting-material, 5-chloro-2-propoxybenzamide, was prepared as follows:

A stirred mixture of 5-chloro-2-hydroxybenzamide (20 g), 1-bromopropane (13.4 ml), potassium iodide (2.49 g) and anhydrous potassium carbonate (24.15 g) in acetone (250 ml) was heated under reflux for 20 hours. The cooled reaction mixture was filtered and the filter cake was washed with acetone. The filtrate and washings were combined and evaporated under reduced pressure to yield a residue which was washed with water, dilute aqueous sodium hydroxide, water and with diethyl ether to yield a crude product (19.85 g). This was recrystallised from acetonitrile, partitioned between chloroform and dilute aqueous sodium hydroxide, and was recrystallised from ethanol to yield 5-chloro-2-propoxybenzamide (16.78 g).

EXAMPLE 47

2-(2-Propoxy-4-methylphenyl)purin-6-one

In a similar manner to Example 44:

a) reaction of 4-methyl-2-propoxybenzamide (11.96 g) with triethyloxonium tetrafluoroborate yielded crude ethyl 4-methyl-2-propoxybenzimidate tetrafluoroborate which on reaction with a saturated solution of ethanolic ammonia and treatment with hydrochloric acid yielded 4-methyl-2-propoxybenzamidine hydrochloride, (8.74 g), m.p. 228–30° C.;

b) reaction of the above amidine (8.70 g) with ethyl cyanoglyoxylate-2-oxime (4.80 g) and sodium ethoxide yielded 2-(4-methyl-2-propoxyphenyl)-4-amino-5-nitrosopyrimidin-6-one, 3.26 g, m.p. 214–6° C.;

c) reaction of the above nitroso compound (3.24 g) with sodium dithionite and sodium bicarbonate yielded on treatment with concentrated sulphuric acid 2-(4-methyl-2propoxyphenyl)-4,5-diaminopyrimidin-6-one sulphate, 4.24 g;

d) reaction of the above diamine sulphate (4.24 g) with formic acid yielded the crude title compound, which was recrystallised from aqueous dimethylformamide to yield the title compound, 1.09 g, m.p. 323–5° C.

The starting-material, 4-methyl-2-propoxybenzamide, was prepared by reacting methyl 4-methyl-salicylate (25.75 g) with ethanolic ammonia to yield 4-methylsalicylamide (12.54 g) which was then reacted with bromopropane, potassium iodide and potassium carbonate in acetone.

EXAMPLE 48

2-(2-Propoxy-5-fluorophenyl)purin-6-one

In a similar manner to Example 44:

a) reaction of 5-fluoro-2-propoxybenzamide (16.40 g) with triethyloxonium tetrafluoroborate yielded ethyl 5-fluoro-2-propoxybenzimidate tetrafluoroborate which on reaction with a saturated solution of ethanolic ammonia yielded 5-fluoro-2-propoxybenzamidine (8.40 g);

b) reaction of the above amidine (5.0 g) with ethyl cyanoglyoxylate-2-oxime (3.35 g) and sodium methoxide (from sodium, 2.17 g, and methanol, 200 ml) yielded 2-(5-fluoro-2-propoxyphenyl)-4-amino-5-nitrosopyrimidin-6-one, 2.2 g, m.p. 220° C. (dec);

c) reaction of the above nitroso compound (1.0 g) with sodium dithionite (1.1 g) yielded 2-(5-fluoro-2-propoxyphenyl)-4, 5-diaminopyrimidin-6-one, 0.75 g, which on reaction with formic acid (10 ml) yielded the crude title compound, (0.63 g) which was recrystallised from aqueous dimethylformamide to yield the title compound, 0.40 g, m.p. 238° C.

The starting-material, 5-fluoro-2-propoxybenzamide, was prepared as follows:

Alkylation of 5-fluoro-2-hydroxyacetophenone (25 g) with bromopropane, potassium iodide and potassium carbonate in acetone yielded 5-fluoro-2-propoxyacetophenone, 20.9 g, m.p. 59–61° C. 5-Fluoro-2-propoxyacetophenone (1 g) was shaken in a solution of bromine (2 ml) in aqueous sodium hydroxide (3.6 g in 30 ml) for 20 minutes, then the stirred mixture was heated at 90° C. for 4 hours. Excess of hypobromite was destroyed with sodium metabisulphite, and the solution was extracted with ether. The organic solution was extracted with 2 Normal sodium hydroxide, the extract acidified and extracted with dichloromethane. Evaporation yielded 5-fluoro-2-propoxybenzoic acid, 0.32 g, m.p. 76–78° C. 5-Fluoro-2-propoxybenzoic acid (29 g) was treated with thionyl chloride to yield the corresponding acid chloride, which was in turn treated with ammonia in ether solution to give 5-fluoro-2-propoxybenzamide, 16.5 g, m.p. 114–116° C.

EXAMPLE 49

2-(2-Propoxy-5-dimethylsulphamoylphenyl)purin-6-one 2-(2-Propoxyphenyl)purin-6-one (0.27 g) was added portionwise with cooling (0° C.) to stirred chlorosulphonic acid (1.25 ml). The reaction mixture was stirred with cooling (0° C.) for 20 minutes and then left at 4° C. for 24 hours. The mixture was washed with dichloromethane (2×20 ml) and the residue was added with cooling (5° C.) to a stirred solution of dimethylamine in industrial methylated spirit (33%, 10 ml). The resulting solution was stirred at ambient temperature for 30 minutes and evaporated under reduced pressure to yield an oil which was treated with water (15 ml) and made basic to pH 9 with potassium carbonate. After standing overnight at ambient temperature a precipitate (0.18 g) was collected, which together with another sample (0.50 g), similarly prepared from 2-(2-propoxyphenyl)purin-6-one (0.68 g) and chlorosulphonic acid (3.5 ml), was recrystallised from aqueous ethanol (with charcoal) to yield the title compound, 0.43 g, m.p. 268–9° C.

EXAMPLE 50

2-(2-Propoxy-5-methylsulphamoylphenyl)purin-6-one

In a similar manner to Example 49 reaction of 2-(2-propoxyphenyl)purin-6-one (0.81 g) with chlorosulphonic acid (4.5 ml), followed by reaction with methylamine in industrial methylated spirit (33%, 50 ml) yielded the title compound, 0.49 g, m.p. 245–246° C. (recrystallised twice from aqueous ethanol).

EXAMPLE 51

5-(2-Ethoxy-5-piperidinoacetylphenyl)-1-methyl-3-n-propyl-1,6-dihydro-7H-pyrazolo[4,3-d]pyrimidin-7-one Piperidine (0.22 ml, 0.0022 mol) was added to a stirred suspension of 5-(5-bromoacetyl-2-ethoxyphenyl)-1-methyl-3-n-propyl-1,6-dihydro-7H-pyrazolo[4,3-d]pyrimidin-7-one (Preparation 8, 0.95 g, 0.0022 mol) and anhydrous potassium carbonate (0.6 g, 0.0044 mol) in acetonitrile (50 ml) at room temperature. After 18 hours the mixture was evaporated under vacuum, the residue dissolved in water (50 ml) and the solution extracted with ethyl acetate (3×30 ml). The organic extracts were combined, washed with brine (3×20 ml), dried ($Na_2SO_4$) and evaporated under vacuum. The resulting yellow solid was chromatographed on silica gel (12 g), using a methanol in dichloromethane elution gradient (0–2% methanol), to give an off-white solid. Crystallisation from ethyl acetate-hexane gave the title compound as an off-white powder (0.27 g, 28%), m.p. 149–151° C. Found: C,66.13; H,6.90; N, 15.95. $C_{24}H_{31}N_5O_5$ requires C,65.88; H,7.14; N,16.01%.

EXAMPLES 52–58

The following Examples were prepared by the procedure of Example 51 using the appropriate amine.

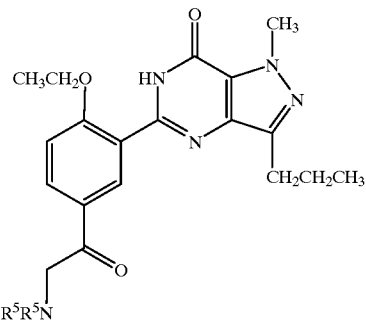

| Example | NR⁵R⁶ | % yield | m.p. (° C.) | Analysis % (theoretical in brackets) C | H | N |
|---|---|---|---|---|---|---|
| 52 | N(CH₂CH₃)₂ | 4 | 120–121 | 65.21 (64.92 | 7.31 7.34 | 16.37 16.46) |
| 53 | (piperazine)NCOCH₃ | 23 | 183–185 | 62.48 (62.48 | 6.62 6.71 | 17.32 17.49) |
| 54 | morpholine | 29 | 159–160 | 63.20 (62.85 | 6.58 6.65 | 15.87 15.94) |
| 55 | 2-methylimidazole | 21 | 202–204 | 61.84 (62.28 | 6.12 6.14 | 18.68 18.95)a |
| 56 | piperazine-NH | 39 | 142–143 | 62.83 (63.00 | 7.09 6.90 | 18.90 19.16) |
| 57 | piperazine-NCH₂CH₂OH | 36 | 135–136 | 62.46 (62.22 | 6.91 7.10 | 17.36 17.41) |
| 58 | 4-hydroxypiperidine | 40 | 151–152 | 63.64 (63.56 | 6.80 6.89 | 15.63 15.44) | a 0.50 H₂O

EXAMPLE 59

5-{2-Ethoxy-5-[1-hydroxy-2-(1-piperazinyl)ethyl] phenyl}-1-methyl-3-n-propyl-1,6-dihydro-7H-pyrazolo[4,3-d]pyrimidin-7-one Sodium borohydride (0.01 g, 0.0027 mol) was added to a stirred suspension of 5-[2-ethoxy-5-(1-piperazinylacetyl) phenyl]-1-methyl-3-n-propyl-1,6-dihydro-7H-pyrazolo[4,3-d]pyrimidin-7-one (0.12 g, 0.0027 mol) in ethanol (10 ml) and the resulting solution stirred at room temperature for 18 hours. The solvent was removed by evaporation under vacuum, the residue suspended in saturated aqueous sodium carbonate solution (50 ml) and this mixture extracted with dichloromethane (3×20 ml). The organic extracts were combined, dried (Na₂SO₄) and evaporated under vacuum to give an oil. Trituration with ether gave a white solid, crystallisation of which from ethyl acetate-hexane gave the title compound as a white powder (0.050 g, 42%), m.p. 139–140° C. Found: C,62.55; H,7.44; N,18.79. C₂₃H₃₂N₆O₃ requires C,62.71; H,7.32; N,19.08%.

EXAMPLES 60–63

The following Examples were prepared by the procedure of Example 59 using the appropriate ketones (Examples 53, 54, 55 and 51 respectively).

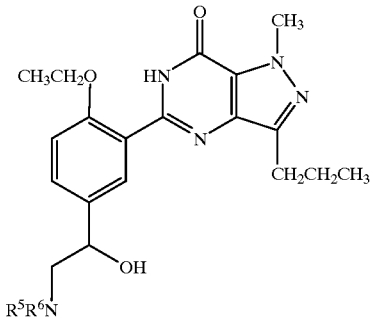

| Example | NR$^5$R$^6$ | % yield | m.p. (° C.) | Analysis % (theoretical in brackets) | | |
|---|---|---|---|---|---|---|
| | | | | C | H | N |
| 60 | N‾NCOCH$_3$ (piperazine-acetyl) | 37 | 139–141 | 61.92 (62.22 | 7.01 7.10 | 17.08 17.42) |
| 61 | N‾O (morpholine) | 69 | 125–127 | 62.23 (62.56 | 7.10 7.08 | 15.53 15.86) |
| 62 | 2-methylimidazole | 77 | 221–222 | 63.68 (63.29 | 6.39 6.47 | 19.17 19.25) |
| 63 | piperidine | 97 | 117–118 | 65.51 (65.58 | 7.57 7.57 | 15.84 15.93) |

EXAMPLE 64

1-Methyl-5-(5-morpholinoacetyl-2-n-propoxyphenyl)-3-n-propyl-1,6-dihydro-7H-pyrazolo[4,3-d]pyrimidin-7-one This compound was prepared from morpholine and 5-(5-bromoacetyl-2-n-propoxyphenyl)-1-methyl-3-n-propyl-1,6-dihydro-7H-pyrazolo[4,3-d]pyrimidin-7-one (Preparation 21), following the procedure of Example 51, and was obtained as white crystals (47%), m.p. 128–129° C. Found: C,63.62; H,7.07; N,15.53. $C_{24}H_{31}N_5O_4$ requires C,63.56; H,6.89; N,15.44%.

EXAMPLE 65

1-Methyl-5-[5-(4-methyl-1-piperazinylacetyl)-2-n-propoxyphenyl]-3-n-propyl-1,6-dihydro-7H-pyrazolo[4,3-d]pyrimidin-7-one This compound was prepared from 4-methylpiperazine and 5-(5-bromoacetyl-2-n-propoxyphenyl)-1-methyl-3-n-propyl-1,6-dihydro-7H-pyrazolo[4,3-d]pyrimidin-7-one (Preparation 21), following the procedure of Example 51, and was obtained as a white solid (27%), m.p. 124–125° C. Found: C,63.96; H,7.19; N,17.80. $C_{25}H_{34}N_6O_3$ requires C,64.36; H,7.34; N,18.01%.

EXAMPLE 66

5-[5-(1-Hydroxy-2-morpholinoethyl)-2-n-propoxyphenyl]-1-methyl-3-n-propyl-1,6-dihydro-7H-pyrazolo[4,3-d]pyrimidin-7-one This compound was prepared from 1-methyl-5-(5-morpholinoacetyl-2-n-propoxyphenyl)-3-n-propyl-1,6-dihydro-7H-pyrazolo[4,3-d]pyrimidin-7-one, following the procedure of Example 59, and was obtained as a white solid (28%), m.p. 104–105° C. Found: C,62.90; H,7.50; N,15.48. $C_{24}H_{33}N_5O_4$ requires C,63.28; H,7.30; N,15.37%.

EXAMPLE 67

5-(5-Acetyl-2-ethoxyphenyl)-1-methyl-3-n-propyl-1,6-dihydro-7H-pyrazolo[4,3-d]-pyrimidin-7-one The title compound was prepared from 4-(5-acetyl-2-ethoxybenzamido)-1-methyl-3-n-propylpyrazole-5-carboxamide (Preparation 15), following the procedure of Preparation 17, and was obtained as a white solid (77%), m.p. 196–198° C. Found: C,64.35; H,6.16; N,15.85. $C_{19}H_{22}N_4O_3$ requires C,64.39; H,6.26; N,15.81%.

EXAMPLE 68

5-(5-Bromo-2-n-propoxyphenyl)-1-methyl-3-n-propyl-1,6-dihydro-7H-pyrazolo[4,3-d]pyrimidin-7-one N-Bromosuccinimide (2.6 g, 0.016 mol) in dimethylformamide (40 ml) was added dropwise to a stirred solution of 5-(2-n-propoxyphenyl)-1-methyl-3-n-propyl-1,6-dihydro-7H-pyrazolo[4,3-d]pyrimidin-7-one (Preparation 10, 4.0 g, 0.010 mol) in dimethylformamide (40 ml) at room temperature. After 7 hours the solvent was removed by evaporation under vacuum, the residue suspended in saturated aqueous sodium carbonate solution, and the resulting solution extracted with ethyl acetate (3×50 ml). The organic extracts were combined, dried ($Na_2SO_4$) and evaporated under vacuum. Trituration of the residue with ether, followed by crystallisation from ethyl acetate-hexane, gave the title compound as white crystals (3.39 g, 68%), m.p. 117–118° C. Found: C,53.15; H,5.03; N,13.78. $C_{18}H_{21}BrN_4O_2$ requires C,53.34; H,5.22; N,13.32%.

EXAMPLE 69

(E)-3-(1-Methyl-7-oxo-3-n-propyl-1,6-dihydro-7H-pyrazolo[4,3-d]pyrimidin-5-yl)-4-n-propoxycinnamic acid t-butyl ester To a solution of 5-(5-bromo-2-n-propoxyphenyl)-1-methyl-3-n-propyl-1,6-dihydro-7H-pyrazolo[4,3-d]pyrimidin-7-one (1.0 g, 0.0025 mol) and triethylamine (0.38 g, 0.0038 mol) in acetonitrile (2 ml), was added palladium (II) acetate (0.03 g, 0.00013 mol), tri-o-tolylphosphine (0.076 g, 0.00025 mol) and t-butyl acrylate (0.48 g, 0.0038 mol). The mixture was heated under reflux for 4 hours, then cooled and evaporated under vacuum. The residue was suspended in water (30 ml) and extraction with dichloromethane (3 x 20 ml) effected. The organic extracts were combined, dried ($Na_2SO_4$) and evaporated under vacuum to give a yellow-green solid. Chromatography on silica gel (12 g), using a methanol in dichloromethane elution gradient (0–2% methanol), followed by crystallisation from ethyl acetate-hexane gave the title compound as a white solid (0.65 g, 58%), m.p. 167–168° C. Found: C,66.47; H,7.00; N,12.31. $C_{25}H_{32}N_4O_4$ requires C,66.35; H,7.13; N,12.38%.

EXAMPLE 70

(E)-3-(1-Methyl-7-oxo-3-n-propyl-1,6-dihydro-7H-pyrazolo[4,3-d]pyrimidin-5-yl)-4-n-propoxycinnamic acid 2N Aqueous sodium hydroxide solution (2.28 ml, 0.0046 mol) was added to a solution of (E)-3-(1-methyl-7-oxo-3-n-propyl-1,6-dihydro-7H-pyrazolo[4,3-d]pyrimidin-5-yl)-4-n-propoxycinnamic acid t-butyl ester (0.40 g, 0.00088 mol) in methanol (2.3 ml) and the mixture was heated under reflux for 18 hours. The methanol was removed by evaporation under vacuum, the residue dissolved in water (25 ml), and the solution extracted with ethyl acetate (4×15 ml). The aqueous layer was separated, acidified to pH 1 with hydrochloric acid, and then extracted with a mixture of methanol and ethyl acetate (3.97,4×20 ml). The organic extracts were combined, dried ($Na_2SO_4$) and evaporated under vacuum, then the residue crystallised from ethyl acetate to give the title compound as a white solid (0.27 g, 77%), m.p. 229–230° C. Found: C,63.64; H,5.98; N,14.14. $C_{21}H_{25}N_4O_4$ requires C,63.46; H,6.34; N,14.10%.

EXAMPLE 71

5-(5(Bromo-2-ethoxyphenyl)-1-methyl-3-n-propyl-1,6-dihydro-7H-pyrazolo[4,3-d]pyrimidin-7-one Bromine (0.93 g, 0.0058 mol) was added dropwise to a stirred solution of 5-(2-ethoxyphenyl)-1-methyl-3-n-propyl-1,6-dihydro-7H-pyrazolo[4,3-d]pyrimidin-7-one (Preparation 17, 1.1 g, 0.00352 mol) in glacial acetic acid (20 ml). The mixture was stirred at 100° C. for 6.5 hours and the solvent was then removed by evaporation under vacuum. The residue was dissolved in a 9:1 mixture of methanol in dichloromethane (50 ml), and the solution washed with saturated aqueous sodium bicarbonate solution (50 ml), water (50 ml) and saturated brine (50 ml), then dried ($MgSO_4$) and evaporated under vacuum. The residue was chromatographed on silica gel (15 g) eluting with a mixture of methanol and dichloromethane (1:99) to give, after crystallisation from acetonitrile, the title compound (0.62 g, 45%), m.p. 157–159° C. Found: C,52.41; H,5.25; N,14.01. $C_{17}H_{19}BrN_4O_2$ requires C,52.18; H,4.89; N,14.32%.

EXAMPLE 72

(E)-4-Ethoxy-3-(1-methyl-7-oxo-3-n-propyl-1,6-dihydro-7H-pyrazolo[4,3-d]pyrimidin-5-yl)cinnamic acid t-butyl ester The title compound was prepared from 5-(5-bromo-2-ethoxyphenyl)-1-methyl-3-n-propyl-1,6-dihydro-7H-pyrazolo[4,3-d]pyrimidin-7-one following the procedure of Example 69 and was obtained as a white crystalline solid (31%), m.p. 179–180° C. Found: C,65.83; H,6.90; N,12.75. $C_{24}H_{30}N_4O_4$ requires C,65.89; H,6.68; N,12.81%.

EXAMPLE 73

(E)-4-Ethoxy-3-(1-methyl-7-oxo-3-n-propyl-1,6-dihydro-7H-pyrazolo[4, 3-d]pyrimidin-5-yl)cinnamic acid The title compound was prepared from (E)-4-ethoxy-3-(1-methyl-7-oxo-3-n-propyl-1,6-dihydro-7H-pyrazolo[4,3-d]pyrimidin-5-yl)cinnamic acid t-butyl ester following the procedure of Example 20 and was obtained as white crystals (66%), m.p. 234–236° C. Found: C,63.01; H,5.59; N,14.62. $C_{20}H_{22}N_4O_4$ requires C,62.82; H,5.80; N,14.65%.

EXAMPLE 74

3-[4-Ethoxy-3-(1-methyl-7-oxo-3-n-propyl-1,6-dihydro-7H-pyrazolo[4,3-d]pyrimidin-5-yl)phenyl]propanoic acid A solution of (E)-4-Ethoxy-3-(1-methyl-7-oxo-3-n-propyl-1,6-dihydro-7H-pyrazolo[4,3-d]pyrimidin-5-yl) cinnamic acid (0.426 g, 0.0011 mol) in a mixture of methanol (28.5 ml), ethyl acetate (100 ml) and water (1.5 ml), was stirred with 5% palladium on charcoal catalyst (0.05 g) under a hydrogen atmosphere at room temperature and pressure for 3 hours. The catalyst was removed by filtration and the solvent removed by evaporation under vacuum. Crystallisation of the residue from ethyl acetate-hexane gave the title compound as beige crystals (0.23 g, 54%), m.p. 165–167° C. Found: C,62.24; H,6.17; N,14.09. $C_{20}H_{24}N_4O_4$ requires C,62.39; H,6.33; N,14.41%.

EXAMPLE 75

(E)-4-Ethoxy-3-(1-methyl-7-oxo-3-n-propyl-1,6-dihydro-7H-pyrazolo[4,3-d]pyrimidin-5-yl)cinnamic acid dimethylamide The title compound was prepared from N,N-dimethylacrylamide and 5-(5-bromo-2-ethoxyphenyl)-1-methyl- 3-n-propyl-1,6-dihydro-7H-pyrazolo[4,3-d]pyrimidin-7-one following the procedure of Example 69 and was obtained, following crystallisation from ethyl acetate-hexane, as colourless crystals (38%), m.p. 219–221° C. Found: C,64.15; H,6.46; N,16.96. $C_{22}H_{27}N_5O_3$ requires C,64.53; H,6.65; N,17.10%.

EXAMPLE 76

3-[4-Ethoxy-3-(1-methyl-7-oxo-3-n-propyl-1,6-dihydro-7H-pyrazolo[4,3-d]pyrimidin-5-yl)phenyl]propanoic acid dimethylamide The title compound was prepared from (E)-4-ethoxy-3-(1-methyl-7-oxo-3-n-propyl-1,6-dihydro-7H-pyrazolo[4,3-d]pyrimidin-5-yl)cinnamic acid dimethylamide following the procedure of Example 74 and, after crystallisation from ethyl acetate-hexane, was obtained as colourless crystals (74%), m.p. 155–157° C. Found: C,64.09; H,7.04; N,16.71. $C_{22}H_{29}N_5O_3$ requires C,64.21; H,7.10; N,17.02%.

EXAMPLE 77

(E)-4-Ethoxy-3-(1-methyl-7-oxo-3-n-propyl-1,6-dihydro-7H-pyrazolo-4,3-d]pyrimidin-5-yl)cinnamonitrile The title compound was prepared from acrylonitrile and 5-(5-bromo-2-ethoxyphenyl)-1-methyl-3-n-propyl-1,6-dihydro-7H-pyrazolo-[4,3-d]pyrimidin-7-one following the procedure of Example 69 and was obtained as off-white crystals (33%). Found: C,65.99; H,5.52; N,19.07. $C_{20}H_{21}N_5O_2$ requires C,66.10; H,5.82; N,19.27%.

EXAMPLE 78

5-[5-(3-Aminopropyl)-2-ethoxyphenyl]-1-methyl-3-n-propyl-1,6-dihydro-7H-pyrazolo[4,3-d]pyrimidin-7-one A solution of (E)-4-ethoxy-3-(l-methyl-7-oxo-3-n-propyl-1,6-dihydro-7H-pyrazolo[4,3-d]pyrimidin-5-yl) cinnamonitrile (0.25 g, 0.00064 mol) in glacial acetic acid (25 ml) was stirred with Raney nickel catalyst (25 mg) under hydrogen at room temperature and at 50 p.s.i. for 3 hours. The resulting mixture was filtered and the filtrate evaporated under vacuum. The residue was partitioned between saturated aqueous sodium carbonate solution (50 ml) and dichloromethane (30 ml), the layers separated and the aqueous phase further extracted with dichloromethane (2×30 ml). The organic solutions were combined, dried ($Na_2SO_4$) and evaporated under vacuum to give a brown solid, crystallization of which from hexane-ethyl acetate gave the title compound as fawn crystals (96 mg, 38%), m.p. 115–117° C. Found C,65.29; H,7.35; N,18.66. $C_{20}H_{27}N_5O_2$ requires C,65.02; H,7.37; N,18.96%.

EXAMPLE 79

4-Ethoxy-3-(1-methyl-7-oxo-3-n-propyl-1,6-dihydro-7H-pyrazolo[4,3-d]pyrimidin-5-yl)benzoic acid n-Butyllithium (2.5 M solution in hexane, 1.53 ml, 0.0038 mol) was added dropwise to a stirred solution of 5-(5-bromo-2-ethoxyphenyl)-1-methyl-3-n-propyl-1,6-dihydro-7H-pyrazolo[4,3-d]pyrimidin-7-one (0.60 g, 0.00074 mol) in dry tetrahydrofuran (25 ml) at −78° C. under a dry nitrogen atmosphere. After 0.3 hour at −78° C., the solution was allowed to warm to −40° C. and carbon dioxide gas was bubbled through the solution. The resulting solution was allowed to warm to room temperature and then poured into water, acidification to pH 3 with 2N hydrochloric acid and extraction with a 9:1 mixture of dichloromethane and methanol (4×50 ml) were then effected. The organic extracts were combined, dried ($MgSO_4$) and evaporated under vacuum to give a colourless solid. Chromatography of this solid on silica gel (20 g), using a methanol in dichloromethane elution gradient (2–5% methanol), gave a solid which was dissolved in a 9:1 mixture of dichloromethane and methanol (50 ml); this solution was then washed with saturated aqueous sodium carbonate solution (50 ml), dried ($MgSO_4$) and evaporated under vacuum to give the title compound as a white powder (0.144 g, 26%), m.p. 285–288° C. Found: C,60.74; H,5.72; N,15.61. $Cl_8H_{20}N_4O_4$ requires C,60.66; H,5.66; N,15.72%.

EXAMPLE 80

5-[2-Ethoxy-5-(4-methylpiperazinylcarbonyl)phenyl]-1-methyl-3-n-propyl-1,6-dihydro-7H-pyrazolo[4,3-d]pyrimidin-7-one A solution of 4-ethoxy-3-(1-methyl-7-oxo-3-n-propyl-1,6-dihydro-7H-pyrazolo[4,3-d]pyrimidin-5-yl)benzoic acid (0.095 g, 0.00027 mol), 1-methylpiperazine (0.265 g, 0.00265 mol), 1-(3-dimethylaminopropyl)-3-ethylcarbodiimide hydrochloride (0.077 g, 0.0004 mol) and 1-hydroxybenzotriazole (0.054 g, 0.0004 mol) in dichloromethane (25 ml) was stirred at room temperature for 18 hours. The reaction solution was washed with water (25 ml), dried ($MgSO_4$) and evaporated under vacuum, and then the resulting residue crystallized from ethyl acetate-hexane to give the title compound as colourless crystals (0.03 g, 25%), m.p. 196–197° C. Found: C,63.12; H,6.81; N,18.96. $C_{23}H_{30}N_6O_3$ requires C,62.99; H,6.90; N,19.16%.

EXAMPLE 81

5-[2-Ethoxy-5-(1-imidazolyl)phenyl]-1-methyl-3-n-propyl-1,6-dihydro-7H-pyrazolo[4,3-d]pyrimidin-7-one A solution of 5-(5-bromo-2-ethoxyphenyl)-1-methyl-3-n-propyl-1,6-dihydro-7H-pyrazolo[4,3-d]pyrimidin-7-one (0.20 g, 0.00051 mol), imidazole (0.172 g, 0.00025 mol), anhydrous potassium carbonate (0.077 g, 0.00056 mol), copper bronze (0.036 g, 0.00057 mol) and iodine (0.015 g, 0.00012 mol) in dimethylformamide (10 ml) was heated under reflux under nitrogen for 4.5 hours, cooled and poured into water (50 ml). This mixture was extracted with a 9:1 mixture of dichloromethane and methanol (6×50 ml) and the extracts combined, dried ($MgSO_4$) and evaporated under vacuum to give a pale brown oil. The oil was chromatographed on silica gel (20 g), eluting with a mixture of dichloromethane, methanol and triethylamine (97.8:2:0.2), to give a yellow solid, crystallization of which from ethyl acetate-hexane gave the title compound as a cream solid (0.073 g, 38%), mp. 193–194° C. Found: C, 63.61; H,5.97; N,22.03. $C_{20}H_{22}N_8O_2$ requires C,63.48; H,5.86; N,22.21%.

EXAMPLE 82

5-[2-Ethoxy-5-(1-methyl-2-imidazolyl)phenyl]-1-methyl-3-n-propyl-1,6-dihydro-7H-pyrazolo[4,3-d]pyrimidin-7-one n-Butyllithium (1.6 M solution in hexane, 9.6 ml, 0.0153 mol) was added to a stirred solution of 1-methyl-imidazole (0.628 g, 0.0077 mol) in dry tetrahydrofuran (10 ml) at −78° C., and the resulting solution stirred for 0.25 hours. A solution of anhydrous zinc chloride (2.08 g, 0.0153 mol) in dry tetrahydrofuran (15 ml) was added, the mixture allowed to warm to room temperature, then 5-(5-bromo-2-ethoxyphenyl)-1-methyl-3-n-propyl-1,6-dihydro-7H-pyrazolo[4,3-d]pyrimidin-7-one (1.0 g, 0.0026 mol) and tetrakis(triphenylphosphine)palladium(0) (0.036 g, 0.031 mol) were added and the mixture heated under reflux for 18 hours. A further quantity of anhydrous zinc chloride (2.08 g, 0.0153 mol) was added and the resulting mixture heated under reflux for a further 60 hours, then cooled, methanol (2 ml) was added and the solvent removed by evaporation under vacuum. The residue was heated with a solution of disodium ethylenediaminetetraacetic acid dihydrate (23.0 g, 0.0618 mol) in water (100 ml) to 100° C. for 0.2 hour, then the resulting solution basified to pH 8 with saturated aqueous sodium carbonate solution and extracted with dichloromethane (6×100 ml). The organic extracts were combined, dried ($Na_2SO_4$) and evaporated under vacuum to give a yellow solid, purification of which by chromatography on silica gel (13 g), using a methanol-dichloromethane elution gradient (0–3% methanol), followed by crystallization from ethyl acetate, gave the title compound as an off-white solid (0.542 g, 53%), m.p. 199–202° C. Found: C,64.45; H,6.27; N,21.56. $C_{21}H_{24}N_6O_2$ requires C,64.27; H,6.16; N,21.42%.

EXAMPLE 83

5-[2-Ethoxy-5-(1-pyridyl)phenyl]-1-methyl-3-n-propyl-1,6-dihydro-7H-pyrazolo[4,3-d]pyrimidin-7-one The title compound was prepared from 2-bromopyridine and 5-(5-bromo-2-ethoxyphenyl)-1-methyl-3-n-propyl-1,6-dihydro-7H-pyrazolo[4,3-d]pyrimidin-7-one, following the procedure described in Example 82, and was obtained as an off-white solid (33%), m.p. 216–218° C. Found: C,67.61; H,5.81; N,17.63. $C_{22}H_{23}N_5O_2$ requires C,67.85; H,5.95; N,17.98%.

EXAMPLE 84

1-Methyl-5-(5-morpholinomethyl-2-n-propoxyphenyl)-3-n-propyl-1,6-dihydro-7H-pyrazolo[4,3-d]pyrimidin-7-one A solution of 5-(5-chloromethyl-2-n-propoxymethyl)-1-methyl-3-n-propyl-1,6-dihydro-7H-pyrazolo[4,3-d]pyrimidin-7-one (Preparation 16, 0.60 g, 0.0016 mol) in 2-butanone (40 ml) was added dropwise to a stirred solution of morpholine (0.42 g, 0.0048 mol) in 2-butanone (40 mol) at 0° C. the solution was then heated under reflux for 16 hours, cooled and evaporated under vacuum. The residue was suspended in water (50 ml) and the suspension extracted with ethyl acetate (3×20 ml). The organic extracts were combined, washed with brine (2×30 ml), dried ($Na_2SO_4$) and evaporated under vacuum. The residue was chromatographed on silica gel (12 g), using an elution gradient of methanol in dichloromethane (0–2% methanol), to give an oil which solidified on trituration with hexane. Crystallization from ethyl acetate-hexane gave the title compound as a colourless solid (0.36 g, 53%), m.p. 106–107° C. Found: C,64.76; H,7.34; N,16.36. $C_{23}H_{31}N_5O_3$ requires C,64.92; H,7.34; N,16.46%.

EXAMPLE 85

1-Methyl-5-[5-(4-methyl-1-piperazinylmethyl)-2-n-propoxyphenyl)-3-n-propyl-1,6-dihydro-7H-pyrazolo[4,3-d]pyrimidin-7-one The title compound was prepared from 5-(5-chloromethyl-2-n-propoxyphenyl)-1-methyl-3-n-propyl-1,6-dihydro-7H-pyrazolo[4,3-d]pyrimidin-7-one and 1-methylpiperazine, following the procedure of Example 84, and was obtained as a colourless solid (36%), m.p. 149–150° C. Found: C,65.68; H,7.33; N,19.10. $C_{24}H_{34}N_6O_2$ requires C,65.73; H,7.81; N,19.16%.

EXAMPLE 86

1-Methyl-5-(5-methyl-2-n-propoxyphenyl)-3-n-propyl-1,6-dihydro-7H-pyrazolo[4,3-d]pyrimidin-7-one A solution of 5-(5-chloromethyl-2-n-propoxymethyl)-1-methyl-3-n-propyl-1,6-dihydro-7H-pyrazolo[4,3-d]pyrimidin-7-one (0.5 g, 0.0013 mol) in ethyl acetate (50 ml) was stirred with 10% palladium on charcoal catalyst under a hydrogen atmosphere at 50 p.s.i. and room temperature. After 1 hour, the mixture was filtered and the filtrate evaporated under vacuum to give a pale green solid. Chromatography on silica gel (4 g) using a methanol in dichloromethane elution gradient gave a white solid, crystallization of which from hexane-ethyl acetate gave the title compound as colourless needles (0.12 g, 26%), m.p. 115–116° C. Found: C,66.66; H,7.12; N,16.55. $C_{19}H_{24}N_4O_2$ requires C,67.04; H,7.11; N,16.46%.

EXAMPLE 87

5-(5-Hydroxymethyl-2-n-propoxypohenyl)-1-methyl-3-n-propyl-1,6-dihydro-7H-pyrazolo[4,3-d]pyrimidin-7-one To a solution of 5-(5-chloromethyl-2-n-propoxymethyl)-1-methyl-3-n-propyl-1,6-dihydro-7H-pyrazolo[4,3-d]pyrimidin-7-one (0.5 g, 0.0013 mol) in dimethyl sulphoxide (10 ml) was added sodium hydroxide (0.26 g, 0.0065 mol) and ethylene glycol (0.41 g, 0.0065 mol). The reaction mixture was heated at 100° C. for 6 hours, allowed to cool and poured into water (50 ml), then the aqueous mixture extracted with ethyl acetate (3×30 ml). The combined extracts were filtered, dried ($Na_2SO_4$) and evaporated under vacuum to provide an oil which was purified by chromatography on silica gel (6 g), using a methanol in dichloromethane elution gradient (0–3% methanol). The solid product was crystallized from hexane-ethyl acetate to afford the title compound as a white solid (2%), mp. 174–175° C. Found: C,63.97; H,6.66; N,15.57. $C_{19}H_{24}N_4O_3$ requires C,64.03; H,6.79; N,15.72%.

EXAMPLE 88

5-(5-Ethoxymethyl-2-n-propoxyphenyl)-1-methyl-3-n-propyl-1,6-dihydro-7H-pyrazolo[4,3-d]pyrimidin-7-one Sodium (0.15 g, 0.0013 mol) was added portionwise to ethanol (40 ml) over 1 hour. 5-(5-Chloromethyl-2-n-propoxymethyl)-1-methyl-3-n-propyl-1,6-dihydro-7H-pyrazolo[4,3-d]pyrimidin-7-one (0.5 g, 0.0013 mol) was then added to the solution and, after 3 days at room temperature, the solvent was removed by evaporation under vacuum. The residual solid was suspended in water (50 ml) and the suspension extracted with ethyl acetate (3×30 ml). The extracts were then combined, dried ($Na_2SO_4$) and evaporated under vacuum to give a green solid. Chromatography on silica gel (6 g) using a methanol in dichloromethane elution gradient gave, after crystallization of the required product from a hexane-ethyl acetate mixture, the title compound as a white solid (0.2 g, 39%) m.p. 89–90° C. Found: C,65.87; H,7.57; N,14.66. $C_{21}H_{28}N_4O_3$ requires C,65.60; H,7.34; N,14.57%.

EXAMPLE 89

5-[5-Hydroxymethyl)-2-n-propoxyphenyl]-1-methyl-3-n-propyl-1,6-dihydro-7H-pyrazolo[4,3-d]pyrimidin-7-one This compound was prepared from 5-(5-chloromethyl-2-n-propoxy-phenyl)-1-methyl-3-n-propyl-1,6-dihydro-7H-pyrazolo[4,3-]pyrimidin-7-one and ethylene glycol following the procedure of Example 88 and was obtained as a white solid (45%), m.p. 101–102° C. Found: C,63.13; H,6.88; N,13.98. $C_{21}H_{28}N_4O_4$ requires C,62.98; H,7.05; N,13.99%.

EXAMPLE 90

1-Methyl-5-[5-(2-morpholinoethoxymethyl)-2-n-propoxyphenyl]-1-methyl-3-n-propyl-1,6-dihydro-7H-pyrazolo[4,3-d]pyrimidin-7-one (a) Methanesulphonyl chloride (0.56 g, 0.0049 mol) was added to a stirred solution of 5-[5-(2-hydroxyethoxymethyl)-2-n-propoxyphenyl]-1-methyl-3-n-propyl-1,6-dihydro-7H-pyrazolo[4,3-d]pyrimidin-7-one (1.8 g, 0.0045 mol) in pyridine (25 ml) at 0° C. After 18 hours at room temperature, the solvent was removed by evaporation under vacuum and the residue partitioned between 2N hydrochloric acid (30 ml) and dichloromethane (30 ml). The aqueous layer was separated and extracted with dichloromethane (2×30 ml), then the organic solutions combined, dried ($Na_2SO_4$) and evaporated under vacuum to give a brown oil. Chromatography on silica gel (12 g) using a methanol in dichloromethane elution gradient (0–3% methanol) gave an oil, trituration of which with hexane, followed by crystallization from hexane-ethyl acetate, gave the required mesylate as white crystals (0.19 g, 9%), m.p. 74–76° C. Found: C,55.71; H,6.25; N,11.69. $C_{22}H_{30}N_4O_6S$ requires C,55.21; H,6,32; N,11.71%.

(b) Morpholine (0.19 g, 0.0021 mol) was added to a solution of the above mesylate, namely 5-[5-(2-methanesulphonyloxyethoxymethyl)-2-n-propoxyphenyl]-1-methyl-3-n-propyl-1,6-dihydro-7H-pyrazolo[4,3-d]pyrimidin-7-one (0.20 g, 0.0021 mol) in acetonitrile (25 ml) and the stirred mixture was heated under reflux for 18 hours. The solvent was removed by evaporation under vacuum, the residue dissolved in saturated aqueous sodium carbonate solution and the solution extracted with ethyl acetate (3×20 ml). The extracts were combined, dried ($Na_2SO_4$) and evaporated under vacuum, and the residue was chromatographed on silica gel (4 g) using an elution gradient of methanol in dichloromethane (0–2% methanol). Evaporation under vacuum of the appropriate fraction, followed by crystallization from hexane, gave the title compound as white crystals (0.098 g, 48%), m.p. 65–66° C. Found: C,64.17; H,7.69; N,14.96. $C_{25}H_{35}N_5O_5$ requires C,63.94; H,7.51; N,14.91%.

EXAMPLE 91

5-(2-Ethoxy-5-methanesulphonamidophenyl)-1-methyl-3-n-propyl-1,6-dihydro-7H-pyrazolo[4,3-d]-pyrimidin-7-one Methanesulphonyl chloride (0.157 g, 0.00137 mol) was added to a stirred solution of 5-(5-amino-2-ethoxyphenyl)-1-methyl-3-n-propyl-1,6-dihydro-7H-pyrazolo[4,3-d]pyrimidin-7-one (0.45 g, 0.00137 mol) in dry pyridine (30 ml) at 0° C. The mixture was stirred for 18 hours at room temperature and then evaporated under vacuum. The residue was suspended in saturated aqueous sodium bicarbonate solution (50 ml) and the mixture extracted with dichloromethane (2×30 ml). The organic extracts were combined, washed with brine (2×30 ml), dried ($Na_2SO_4$) and evaporated under vacuum. The residue was triturated with ether, chromatographed on silica gel (12 g), eluting with a 98.5:1.5 mixture of dichloromethane and methanol, and the required product crystallized from ethyl acetate-hexane to give the title compound as a white powder (0.32 g, 58%), m.p. 205–206° C. Found: C,53.63; H,5.66; N,17.24. $C_{18}H_{23}N_5O_4S$ requires C,53.32; H,5.72; N,17.27%.

EXAMPLE 92

5-[2-Ethoxy-5-(3-morpholinopropylsulphonamido) phenyl)-1-methyl-3-n-propyl-1,6-dihydro-7H-pyrazolo[4,3-d]pyrimidin-7-one The title compound was prepared from 5-(5-amino-2-ethoxyphenyl)-1-methyl-3-n-propyl-1,6-dihydro-7H-pyrazolo[4,3-d]pyrimidin-7-one and 3-morpholinopropylsulfonyl chloride, following the procedure of Example 91, and was obtained as brown crystals (14%), m.p. 157–159° C. Found: C,55.42; H,6.53; N,16.01. $C_{24}H_{34}N_6O_5S$ requires C,55.58; H,6.61; N,16.21%.

EXAMPLE 93

5-[2-Ethoxy-5-(4-methyl-1-piperazinyl) sulphonamidophenyl)-1-methyl-3-n-propyl-1,6-dihydro-7H-pyrazolo[4,3-d]pyrimidin-7-one The title compound was prepared from 4-methyl-1-piperazinylsulphonyl chloride and 5-(5-amino-2-ethoxyphenyl)-1-methyl-3-n-propyl-1,6-dihydro-7H-pyrazolo[4,3-d]pyrimidin-7-one, following the procedure of Example 91, and was obtained as an orange powder (13%), m.p. 152–153° C. Found: C,54.32; H,6.38; N,19.88. $C_{22}H_{31}N_7O_4S$ requires C,53.97; H,6.38; N,20.03%.

EXAMPLE 94

5-[5-(4-Benzyl-1-piperazinylsulphonamidophenyl)-2-ethoxy-1-methyl-3-n-propyl-1,6-dihydro-7H-pyrazolo(4,3-d]pyrimidin-7-one 4-Benzyl-1-piperazinylsulphonyl chloride (Preparation 29, 0.9 g, 0.0029 mol) was added to a stirred solution of 5-(5-amino-2-ethoxy-phenyl)-1-methyl-3-n-propyl-1,6-dihydro-7H-pyrazolo[4,3-d]pyrimidin-7-one (0.94 g, 0.0029 mol), 4-dimethylaminopyridine (0.050 g, 0.00041 mol) and triethylamine (1.09 g, 0.0108 mol) in dichloromethane (50 ml). The solution was stirred at room temperature for 48 hours and then evaporated under vacuum. The residue was suspended in saturated aqueous sodium bicarbonate solution (50 ml) and the suspension extracted with dichloromethane (3×30 ml). The organic extracts were combined, washed successively with saturated aqueous sodium bicarbonate solution (2×20 ml) and brine (3×20 ml), dried ($Na_2SO_4$) and evaporated under vacuum. The residue was chromatographed on silica gel (20 g) using a methanol in dichloromethane elution gradient (0–4% methanol), and the required product crystallized from ethyl acetate-hexane to give the title compound as an off-white powder (0.185 g, 11%). Found: C,58.30; H,6.20; N,16.80. $C_{28}H_{35}N_7O_4S1$ 1 9,5$H_2O$ requires, C,58.52; H,6.31; N,17.06%.

EXAMPLE 95

1-Methyl-3-n-propylpyrazole-5-carboxylic acid ethyl ester

A mixture of 3-n-propylpyrazole-5-carboxylic acid ethyl ester (24.1 g, 0.132 mol) (prepared by the method of Chem. Pharm. Bull., 1984, 32, 1568) and dimethyl sulphate (16.8 g, 0.133 mol) were heated to 90° C. for 2.5 hours. The mixture was dissolved in dichloromethane and the solution washed with sodium carbonate solution. The organic phase was separated, dried ($MgSO_4$) and evaporated under vacuum to give a solid. Chromatography on silica gel (300 g), eluting with dichloromethane gave the product as a colourless oil (20.4 g, 79%). Rf 0.8 (silica; dichloromethane, methanol, acetic acid; 80:20:1).

EXAMPLE 96

1-Methyl-3-n-propylpyrazole-5-carboxylic acid

1-Methyl-3-n-propylpyrazole-5-carboxylic acid ethyl ester (20.2 g, 0.10 mol) was suspended in 6N aqueous sodium hydroxide solution (50 ml, 0.30 mol). The mixture was heated to 80° C. for 2 hours then diluted with water (50 ml) and acidified with concentrated hydrochloric acid (25 ml). Filtration gave the carboxylic acid as pale brown crystals (12.3 g, 71%), m.p. 150–154° C. Found: C,56.99; H,7.25; N,16.90. $C_8H_{12}N_2O_2$ requires C,57.13; H,7.19; N,16.66%.

EXAMPLE 97

1-Methyl-4-nitro-3-n-propylpyrazole-5-carboxylic acid

1-Methyl-3-n-propylpyrazole-5-carboxylic acid (12.1 g, 0.072 mol) was added portionwise to a mixture of oleum (13 ml) and fuming nitric acid (11 ml), keeping the temperature below 60° C. After the addition, the mixture was heated at 60° C. overnight and then cooled to room temperature before being poured onto ice. Filtration of the precipitate gave the nitropyrazole as a white solid (11.5 g, 75%), m.p. 124–127° C. Found: C,45.43; H,5.22; N,19.42. $C_8H_{11}N_3O_4$ requires C,45.57; H,5.20; N,19.71%.

EXAMPLE 98

1-Methyl-4-nitro-3-n-propylpyrazole-5-carboxamide

1-Methyl-4-nitro-3-n-propylpyrazole-5-carboxylic acid (11.3 g, 0.053 mol) was added to thionyl chloride (50 ml) and the resulting mixture heated under reflux for 3 hours. The reaction mixture was then cooled and excess thionyl chloride removed by evaporation under vacuum. The oily residue was dissolved in acetone (50 ml) and the solution cautiously added to a mixture of ice (50 g) and concentrated aqueous ammonium hydroxide solution (50 ml). The precipitate was collected by filtration to provide the pyrazole-carboxamide as a pale yellow solid (8.77 g, 78%), m.p. 141–143° C. Found: C,45.22; H,5.71; N,26.12. $C_8H_{12}N_4O_3$ requires C,45.28; H,5.70; N,26.40%.

EXAMPLE 99

4-Amino-1-methyl-3-n-propylpyrazole-5-carboxamide

1-Methyl-4-nitro-3-n-propylpyrazole-5-carboxamide (3.45 g, 16.2 mmol) and stannous chloride dihydrate (18.4 g, 81 mmol) were suspended in ethanol and the mixture heated under reflux for 2 hours. The resulting solution was cooled to room temperature, basified to pH 9 by the addition of 2N aqueous sodium hydroxide solution and extracted with dichloromethane (3×150 ml). The organic extracts were combined, dried ($MgSO_4$) and evaporated under vacuum. Trituration of the residue with ether gave the aminopyrazole as an off-white solid (2.77 g, 94%), m.p. 98–101° C. Found: C,52.84; H,7.81; N,30.38. $C_8H_{14}N_4O$ requires C,52.73; H,7.74; N,30.75%.

EXAMPLE 100

4-(2-Ethoxybenzamido)-1-methyl-3-n-propylpyrazole-5-carboxamide

A solution of 2-ethoxybenzoyl chloride (6.1 g, 33.0 mmol) in dichloromethane (50 ml) was added to a stirred solution of 4-amino-1-methyl-3-n-propylpyrazole-5-carboxamide (3.0 g, 16.4 mmol), 4-dimethylaminopyridine (0.02 g, 0.164 mmol) and triethylamine (3.34 g, 33.0 mmol) in dichloromethane (50 ml) at 0° C. The resulting mixture was allowed to warm to room temperature and stirred for a further 2 hours. The solvent was evaporated under vacuum, the residue dissolved in a 19:1 mixture of dichloromethane and methanol (250 ml), and then the solution washed with 1N hydrochloric acid (100 ml), dried ($MgSO_4$) and evaporated under vacuum. The crude material was chromatographed on silica gel (200 g), eluting with a 97:3 mixture of dichloromethane and methanol, to give a pink solid; crystallisation from ethyl acetate-hexane gave the pyrazole-3-carboxamide as a pale pink solid (2.2 g, 40%), m.p. 153–155° C. Found: C,61.66; H,6.77; N,16.95. $C_{17}H_{22}N_4O_3$ requires C,61.80; H,6.71; N,16.96%.

EXAMPLE 101

5-(2-Ethoxyphenyl)-1-methyl-3-n-propyl-1,6-dihydro-7H-pyrazolo[4,3-d]pyrimidin-7-one 4-(2-Ethoxybenzamido)-1-methyl-3-n-propylpyrazole-5-carboxamide (223 g, 0.676 mol) was added portionwise to a solution of sodium hydroxide (54 g, 1.35 mol) and 30% hydrogen peroxide solution (224 ml) in water (2000 ml). Ethanol (700 ml) was added and the resulting mixture heated under reflux for 2.5 hours, cooled, then evaporated under vacuum. The resulting solid was treated with 2N hydrochloric acid (380 ml), with external cooling, and the mixture was extracted with dichloromethane (1×700 ml, 3×200 ml). The combined organic extracts were washed successively with saturated aqueous sodium carbonate solution (3×400 ml) and brine (300 ml), then dried ($Na_2SO_4$) and evaporated under vacuum.

Chromatography of the residue on silica gel (1000 g), using a methanol in dichloromethane elution gradient (0-1), followed by trituration of the crude product with ether (300 ml), gave the title compound as a colourless solid (152.2 g, 72%), m.p. 143–146° C. Found: C,65.56; H,6.44; N,18.14. $C_{17}H_{20}N_4O_2$ requires C,65.36; H,6.45; N,17.94%.

EXAMPLE 102

5-(5-Chlorosulphonyl-2-ethoxyphenyl)-1-methyl-3-n-propyl-1,6-dihydro-7H-pyrazolo[4,3-d]pyrimidin-7-one 5-(2-Ethoxyphenyl)-1-methyl-3-n-propyl-1,6-dihydro-7H-pyrazolo[4,3-d]pyrimidin-7-one (10.0 g, 32.1 mmol) was added portionwise to chlorosulphonic acid (20 ml) at 0° C. under a nitrogen atmosphere. After being stirred overnight, the reaction solution was cautiously added to ice-water (150 ml) and the aqueous mixture extracted with a 9:1 mixture of dichloromethane and methanol (4×100 ml). The combined extracts were dried ($Na_2SO_4$) and evaporated under vacuum to give the required sulphonyl chloride as a white solid (12.8 g, 97%), m.p. 179–181° C. Found: C,50.07; H,4.71; N,13.29. $C_{17}H_{19}ClN_4O_4S$ requires C,49.70; H,4.66; N,13.64%.

EXAMPLE 103

5-[2-Ethoxy-5-(4-carbamoylpiperidinylsulphonyl)phenyl-1-methyl-3-n-propyl-1,6-dihydro-7H-pyrazolo[4,3-d]-pyrimidin-7-one 4-Carbamoylpiperidine (703 mg, 5.50 mmol) was added to a stirred suspension of 5-(5-chlorosulphonyl-2-ethoxyphenyl)-1-methyl-3-n-propyl-1,6-dihydro-7H-pyrazolo[4,3-d]pyrimidin-7-one (750 mg, 1.80 mmol) in ethanol (50 ml) at room temperature. The resulting mixture was stirred for 4 days before removing the solvent by evaporation under vacuum. The residue was dissolved in a 9:1 mixture of dichloromethane and methanol (100 ml) and the solution washed with saturated aqueous sodium carbonate solution (100 ml). The aqueous phase was further extracted with dichloromethane-methanol mixtures (3×100 ml) and all the organic fractions were combined, dried ($MgSO_4$) and evaporated under vacuum to give a solid. Crystallisation from a mixture of methanol-dimethylformamide gave the title sulphonamide as an off-white solid (446 mg, 49%), m.p. 274–276° C. Found: C,55.36; H,6.01; N,16.65. $C_{23}H_{29}N_6O_5S$ requires C,55.08; H,5.83; N,16.75%.

EXAMPLES 104–109

The following compounds were prepared by the procedure of Example 103 using the appropriate amine.

| Example | R⁴ | % yield | m.p. (°C.) | Analysis % (Theoretical in brackets) C | H | N |
|---|---|---|---|---|---|---|
| 104 | —SO₂N(piperazinyl)NH | 51 | 161–162 | 54.82 (54.77 | 6.13 6.13 | 17.95 18.25) |
| 105 | —SO₂N(piperazinyl)N–CH₂CH₂OH | 79 | 194–196 | 54.63 (54.75 | 6.47 6.39 | 16.50 16.65) |
| 106 | —SO₂N(piperazinyl)NCH₃ | 88 | 187–189 | 55.61 (55.68 | 6.23 6.37 | 17.74 17.71) |
| 107 | —SO₂N(piperazinyl)N(CH₃)₂ | 21 | 187–188 | 57.48 (57.35 | 6.74 6.82 | 16.47 16.72) |
| 108 | —SO₂N(piperazinyl)N–CH(CH₃)₂ | 74 | 209–212 | 57.64 (57.35 | 6.66 6.82 | 16.81 16.72) |
| 109 | —SO₂N(piperazinyl)NCSNH₂ | 18 | 229–230 | 51.25 (50.85 | 5.56 5.63 | 18.92 18.87) |

EXAMPLE 110

5-{2-Ethoxy-5-[4-(methylthioimidoyl)piperazinylsulphonyl]-phenyl}-1-methyl-3-n-propyl-1,6-dihydro-7H-pyrazolo[4,3-d]pyrimidin-7-one hydroiodide A mixture of 5-[2-ethoxy-5-(4-thiocarbamoylpiperazinylsulphonyl)phenyl]-1-methyl-3-n-propyl-1,6-dihydro-7H-pyrazolo[4,3-d]pyrimidin-7-one (0.78 g, 1.5 mmol), methyl iodide (426 mg. 3.0 mmol) and methanol (20 ml) was stirred under reflux for 2 hours, then allowed to cool. The resulting white solid was removed by filtration and crystallised from ethyl acetate-methanol to give the title compound as colourless crystals (0.70 g, 71%), m.p. 227–228° C. Found: C, H, 4.79; N, 14.42. $C_{23}H_{31}N_7O_4S_2$; HI requires C, H, 4.88; N, 14.82%.

EXAMPLE 111

5-{2-Ethoxy-5-[4-(methylamidino)piperazinylsulphonyl]phenyl}-1-methyl-3-n-propyl-1,6-dihydro-7H-pyrazolo-[4,3-d]pyrimidin-7-one hydroiodide 5-{2-Ethoxy-5-[4-(methylthioimidoyl)-piperazinylsulphonyl]phenyl}-1-methyl-3-n-propyl-1,6-dihydro-7H-pyrazolo[4,3-d]pyrimidin-7-one hydroioide (0.5 g, 0.75 mmol) was added to a 33% solution of methylamine in ethanol (20 ml) and the mixture stirred at room temperature for 18 hours. The solution was evaporated under vacuum and the reside triturated with ether. Chromatography of the resulting solid on silica gel (10 g), using a methanol in dichloromethane elution gradient (0–4%), followed by trituration of the crude product with ether, gave a light brown powder. Crystallisation from ethyl acetate-methanol gave the title compound as colourless crystals (112 mg, 23%), m.p. 253–255° C. Found: C, 42.90; H, 5.09; N, 17.41. $C_{23}H_{32}N_8O_4S$; HI requires C, 42.86; H, 5.16; N, 17.39%.

EXAMPLE 112

1-Methyl-4-(2-n-propoxybenzamido)-3-n-propylpyrazole-5-carboxamide

This amide was prepared from 2-n-propoxybenzoyl chloride following the procedure described in Example 100 and was obtained as a pink solid (63%), m.p. 148–149° C. Found: C, 62.97; H, 7.00; N, 16.29. $C_{18}H_{24}N_4O_3$ requires C, 62.77; H, 7.02; N, 16.27%.

EXAMPLE 113

1-Methyl-5-(2-n-propoxyphenyl)-3-n-propyl-1,6-dihydro-7H-pyrazolo[4,3-d]pyrimidin-7-one 1-Methyl-4-(2-n-propoxybenzamido)-3-n-propylpyrazole-5-carboxamide (0.34 g, 0.99 mmol) was added to a stirred mixture of 30% hydrogen peroxide solution (1.0 ml), potassium carbonate (0.54 g, 3.92 mmol), water (10 ml) and ethanol (5 ml). The mixture was heated under reflux for 38 hours and then evaporated under vacuum. The residue was suspended in water (20 ml), then the mixture acidified with 2N hydrochloric acid and extracted with dichloromethane (3×20 ml). The extracts are combined, dried ($Na_2SO_4$) and evaporated under vacuum. The resulting residue was chromatographed on silica gel (6 g), using a methanol in dichloromethane elution gradient (0.0–1.0%), to give an oil, successive trituration of which with ether gave the required product as a white solid (0.19 g, 59%), m.p. 111–114° C. Found: C, 66.26; H, 6.92; N, 17.15. $C_{18}H_{22}N_4O_2$ requires C, 66.23; H, 6.80; N, 17.17%.

EXAMPLE 114

5-(5–Chlorosulphonyl-2-n-propoxyphenyl)-1-methyl-3-n-propyl-1,6-dihydro-7H-pyrazole[4,3-d]pyrimidin-7-one This sulphonyl chloride was prepared from 5-(2-n-propoxyphenyl)-1-methyl-3-n-propyl-1,6-dihydro-7H-pyrazolo[4,3-d]pyrimidin-7-one following the procedure of Example 102 and was obtained as a white solid (92%). Found: C, 51.26; H, 5.02; N, 12.90. $C_{18}H_{21}ClN_4O_4S$ requires C, 50.88; H, 4.98; N, 13.19%.

EXAMPLE 115

1-Methyl-5-[5-(piperazinylsulphonyl)-2-n-propoxyphenyl]-3-n-propyl-1,6-dihydro-7H-pyrazolo[4,3-d]pyrimidin-7-one This sulphonamide was prepared from piperazine and 5-(5-chlorosulphonyl-2-n-propoxyphenyl)-1-methyl-3-n-propyl-1,6-dihydro-7H-pyrazolo[4,3-d]pyrimidin-7-one following the procedure of Example 103 and was obtained as a white solid (70%), m.p. 185–186° C. Found: C, 56.17; H, 6.38; N, 17.65. $C_{22}H_{30}N_6O_4S$ requires C, 55.67; H, 6.37; N, 17.71%.

EXAMPLE 116

5-{5-[4-(2-Hydroxyethyl)piperazinylsulphonyl]-2-n-propoxyphenyl}-1-methyl-3-n-propyl-1,6-dihydro-7H-pyrazolo[4,3-d]pyrimidin-7-one This sulphonamide was prepared from N-(2-hydroxyethyl)piperazine and 5-(5-chlorosulphonyl-2-n-propoxyphenyl)-1-methyl-3-n-propyl-1,6-dihydro-7H-pyrazolo[4,3-d]pyrimidin-7-one following the procedure of Example 103 and was obtained as colourless needles (66%), m.p. 158–159° C. Found: C, 55.83; H, 6.58; N, 16.13. $C_{24}H_{34}N_6O_5S$ requires C, 55.58; H, 6.61; N, 16.20%.

EXAMPLE 117

4-(2-Allyloxybenzamido)-1-methyl-3-n-propylpyrazole-5-carboxamide

A solution of 2-allyloxybenzoyl chloride (3.93 g, 0.02 mol) in dichloromethane (20 ml) was added dropwise to a stirred, partial solution of 4-amino-1-methyl-3-n-propylpyrazole-5-carboxamide (3.64 g, 0.02 mol) in pyridine (50 ml), and the resulting mixture stirred at room temperature overnight in a dry atmosphere. The solvent was evaporated under vacuum and the residue partitioned between dichloromethane (50 ml) and saturated aqueous sodium carbonate solution (50 ml). The organic layer was separated and the aqueous layer exhaustively extracted with further dichloromethane. The combined organic solutions were washed with 2M Hcl (3×30 ml), then brine (1×30 ml), and dried ($Na_2SO_4$). After filtration and evaporation under vacuum of the filtrate, the crude product was crystallised from ethyl acetate to give the title compound (4.525 g, 66%), m.p. 132–134° C. Found: C, 63.49; H, 6.42; N, 16.33. $C_{18}H_{22}N_4O_3$ requires C, 63.14; H, 6.48; N, 16.36%.

EXAMPLE 118

5-(2-Allyloxyphenyl)-1-methyl-3-n-propyl-1,6-dihydro-7H-pyrazolo[4,3-d]pyrimidin-7-one A mixture of 4-(2-allyloxybenzamido)-1-methyl-3-n-propylpyrazole-5-carboxamide (1.2 g, 0.0035 mol), sodium hydroxide (0.70 g, 0.018 mol), water (34 ml) and ethanol (8 ml) was refluxed for 5 hours. After cooling, the solution was exhaustively extracted with ethyl acetate. The combined extracts were washed with brine (30 ml), dried ($Na_2SO_4$), filtered and the solvent evaporated under vacuum to give a crude product which was crystallised from ethyl acetate/hexane to afford the title compound (0.476 g, 37%), m.p. 116–119° C. Found: C, 67.00; H, 6.21; N, 17.23. $C_{18}H_{20}N_4O_2$ requires C, 66.65; H, 6.21; N, 17.27%.

EXAMPLE 119

5-(2-Hydroxyphenyl)-1-methyl-3-n-propyl-1,6-dihydro-7H-pyrazolo[4,3-d]pyrimidin-7-one A mixture of 5-(2-allyloxyphenyl)-1-methyl-3-n-propyl-1,6-dihydro-7H-pyrazolo[4,3-d]pyrimidin-7-one (0.25 g, 0.0008 mol), phenol (0.145 g, 0.0015 mol), piperidine (0.131 g, 0.0015 mol) and tetrakis-(triphenylphosphine) palladium(0) (0.046 g, 0.00004 mol) in absolute ethanol (5 ml) was refluxed overnight under nitrogen. The mixture was allowed to cool, the solvent evaporated under vacuum and the residue dissolved in ethyl acetate (40 ml). This solution was washed with water (3×10 ml), 1M HCl (3×10 ml) and brine (1×10 ml). After drying ($Na_2SO_4$) and filtration, the filtrate was evaporated under vacuum to give the crystallisation from ethyl acetate/pentane, m.p 233–238° C. Found: C, 63.17; H, 5.65; N, 19.52. $C_{15}H_{16}N_4O_2$ requires C, 63.36; H, 5.67; N, 19.71%.

EXAMPLE 120

5-(5–Chlorosulphonyl-2-hydroxyphenyl)-1-methyl-3-n-propyl-1,6-dihydro-7H-pyrazolo[4,3-d]pyrimidin-7-one 5-(2-Hydroxyphenyl)-1-methyl-3-n-propyl-1,6-dihydro-7H-pyrazolo[4,3-d]pyrimidin-7-one (0.239 g, 0.00084 mol) was added, in portions, to stirred chlorosulphonic acid (3 ml) cooled to 0° C. under a nitrogen atmosphere, and the resulting deep red solution stirred at room temperature for 18 hours. The reaction mixture was then added dropwise, with care, to stirred ice/water to give a brown solid. The latter mixture was extracted with dichloromethane (3×30 ml), the combined extracts dried ($Na_2SO_4$) and filtered, and the filtrate evaporated under vacuum to give a brown solid (0.24 g, 75%), used in the next step without further purification; Rf 0.3 (silica; dichloromethane, methanol; 95:5).

EXAMPLE 121

5-[2-Hydroxy-5-(4-methylpiperazinylsulphonyl)phenyl]-1-methyl-3-n-propyl-1,6-dihydro-7H-pyrazolo[4,3-d]pyrimidin-7-one A solution of 5-(5-chlorosulphonyl-2-hydroxyphenyl)-1-methyl-3-n-propyl-1,6-dihydro-7H-pyrazolo[4,3-d]pyrimidin-7-one (0.235 g, 0.0006 mol) and N-methylpiperazine (0.5 ml, 0.0045 mol) in ethanol (40 ml) was stirred at room temperature for 18 hours. The solution was evaporated under vacuum and the residue partitioned between ethyl acetate (40 ml) and water (40 ml). The fine precipitate was filtered off, washed with water then ethyl acetate, and crystallised from ethyl acetate/DMF to give the title compound as an off-white powder (0.260 g, 49%), m.p.. 283–284° C. Found: C, 53.53; H, 5.89; N, 18.40. $C_{20}H_{26}N_6O_4S$ requires C, 53.80; H, 5.87; N, 18.82%.

EXAMPLE 122

5-[2-Allyloxy-5-(4-methylpiperazinylsulphonyl)phenyl]-1-methyl-3-n-propyl-1,6-dihydro-7H-pyrazolo[4,3-d]-pyrimidin-7-one Allyl bromide (0.02 g, 0.00023 mol) was added to a stirred suspension of 5-[2-hydroxy-5-(4-methylpiperazinylsulphonyl)phenyl]-1-methyl-3-n-propyl-1,6-dihydro-7H-pyrazolo[4,3-d]pyrimidin-7-one (0.103 g, 0.00023 mol) and potassium carbonate (0.032 g, 0.00023 mol) in 2-butanone (10 ml) and the mixture heated under reflux for 8 hours. After cooling, the reaction mixture was evaporated under vacuum and the residue suspended in water (20 ml). The aqueous suspension was extracted with ethyl acetate (3×20 ml), the combined extracts dried ($Na_2SO_4$) and, after filtration, evaporated under vacuum to give an oil. Column chromatography on silica gel (2 g) using a methanol in dichloromethane elution gradient (0–3%), followed by evaporation under vacuum of appropriate fractions, gave a semi-solid which was dissolved in acetone; evaporation under vacuum of the solution gave the title compound (0.011 g, 10%), m.p. 151–153° C., Rf 0.5 (silica; dichloromethane, methanol; 95:5), m/e 87 ($M^+1$)

EXAMPLE 123

4-(2-Ethoxybenzamido)-1,3-dimethylpyrazole-5-carboxamide

This amide was prepared from 4-amino-1,3-dimethylpyrazole-5-carboxamide (prepared by the method of J. Med. Chem 1987, 30, 91), following the procedure of Example 100, and was obtained as a white solid (81%), m.p. 178–181° C. Found: C, 59.89; H, 6.05; N, 18.44. $C_{15}H_{18}N_4O_3$ requires C, 59.59; H, 6.00; N, 18.53%.

EXAMPLE 124

5-(2-Ethoxyphenyl)-1,3-dimethyl-1,6-dihydro-7H-pyrazolo]4,3-d]pyrimidin-7-one 4-(2-Ethoxybenzamido)-1,3-dimethylpyrazole-5-carboxamide (1.6 g, 5.29 mmol) was added to polyphosphoric acid (50 g) and the mixture heated to 140° C. for 6 hours. The solution was cooled, poured into ice-water (100 ml), and then the mixture was basified with 10% aqueous sodium hydroxide solution and extracted with dichloromethane (3×100 ml). The organic extracts were combined, dried ($MgSO_4$) and evaporated under vacuum. The residue was chromatographed on silica gel eluting with a 97:3 mixture of dichloromethane and methanol. Crystallisation of the crude product from aqueous ethanol gave the title compound as a colourless solid, m.p. 201–204° C. Found: C, 63.43; H, 5.57; N, 19.35. $C_{15}H_{16}N_4O_2$ requires C, 63.36; H, 5.67; N, 19.71%.

EXAMPLE 125

5-(5–Chlorosulphonyl-2-ethoxyphenyl)-1,3-dimethyl-1,6-dihydro-7H-pyrazolo[4,3-d]-pyrimidin-7-one This sulphonyl chloride was prepared from 5-(2-ethoxyphenyl)-1,3-dimethyl-1,6-dihydro-7H-pyrazolo-[4,3-d]pyrimidin-7-one, following the procedure of Example 102, and was obtained in quantitative yield as a white solid. Rf 0.3 (silica:ether). It was used without further purification.

EXAMPLES 126–128

The following compounds were prepared from 5-(2-ethoxyphenyl)-1,3-dimethyl-1,6-dihydro-7H-pyrazolo-[4,3-d]pyrimidin-7-one and the appropriate amine following the procedure of Example 103.

| Example | $R^4$ | % yield | m.p. (° C.) | Analysis % (Theoretical in brackets) | | |
|---|---|---|---|---|---|---|
| | | | | C | H | N |
| 126 | —SO₂N(piperazinyl)NCH₃ | 68 | 225–226 | 53.88 (53.79 | 5.81 5.87 | 18.42 18.82) |
| 127 | —SO₂N(piperazinyl)NH | 68 | 240–242 | 53.07 (52.76 | 5.77 5.59 | 19.27 19.43) |
| 128 | —SO₂N(piperazinyl)N∼OH | 62 | 228–229 | 53.23 (52.93 | 5.87 5.92 | 17.72 17.63) |

EXAMPLE 129

3-n-Propylpyrazole-5-carboxylic acid (prepared by the method of Chem. Pharm. Bull. 1984, 32, 1568), was nitrated following the procedure of Example 97, to give the title compound as a colourless solid (75%), m.p. 169–173° C. Found: C, 42.35; H, 4.56; N, 21.07. $C_7H_9N_3O_4$ requires C, 42.21; H, 4.55; N, 21.10%.

EXAMPLE 130

4-Nitro-3-n-propylpyrazole-5-carboxamide

A mixture of 4-nitro-3-n-propylpyrazole-5-carboxylic acid (7.8 g, 39.2 mmol) and thionyl chloride (35 ml) was heated under reflux for 3 hours. The solvent was removed by evaporation under vacuum and the solid residue was added portionwise to aqueous ammonium hydroxide solution (40 ml) at 0C. The mixture was then diluted with water (60 ml) and extracted with a 9:1 mixture of dichloromethane and methanol (3×100 ml). The organic fractions were combined, dried ($MgSO_4$) and evaporated under vacuum, and the residue crystallised from ethanol to give the carboxamide as a colourless solid (1.0 g, 13%), m.p. 202–206° C. Found: C, 42.35; H, 5.01; N, 28.38. $C_7H_{10}N_4O_3$ requires C, 42.42; H, 5.09; N, 28.27%.

EXAMPLE 131

4-Amino-3-n-propylpyrazole-5-carboxamide

A solution of 4-nitro-3-n-propylpyrazole-5-carboxamide (198 mg, 1.0 mmol) in methanol (5 ml) was added dropwise to a mixture of sodium borohydride (113 mg, 2.97 mmol), 10% palladium on carbon (5 mg) and water (3 ml). The mixture was stirred at room temperature for 3 hours, filtered and the solvent removed by evaporation under vacuum. Crystallisation of the residue from ethyl acetate-methanol gave the title compound as an off-white solid (61 mg, 36%), m.p. 196–201° C. Rf 0.4 (silica; dichloromethane, methanol, ammonium hydroxide; 90:10:1). Found: C, 48.96; H, 6.98; N, 32.08. $C_7H_{12}N_4O$ requires C, 49.98; H, 7.19; N, 33.31%.

EXAMPLE 132

4-(2-Ethoxybenzamido)-3-n-propylpyrazole-5-carboxamide

The title amide was prepared from 4-amino-3-n-propylpyrazole-5-carboxamide following the procedure of Example 100, and was obtained as a white solid (64%), m.p. 209–211° C. Found: C, 60.73; H, 6.41; N, 17.80. $C_{16}H_{20}N_4O_3$ requires C, 60.74; H, 6.37; N, 17.71%.

EXAMPLE 133

5-(2-Ethoxyphenyl)-3-n-propyl-1,6-dihydro-7H-pyrazolo[4,3-d]pyrimidin-7-one

The title compound was prepared from 4-(2-ethoxybenzamido)-3-n-propyl-pyrazolo-5-carboxamide following the procedure of Example 124 and was obtained as a white solid (16%), m.p. 199–210° C. Found: C, 64.44; H, 6.19; N, 18.44%. $C_{16}H_{18}N_4O_2$ requires C, 64.41; H, 6.08; N, 18.78%.

EXAMPLE 134

5-(5-Chlorosulphonyl-2-ethoxyphenyl)-3-n-propyl-1,6-dihydro-7H-pyrazolo[4,3-d]pyrimidin-7-one The title sulphonyl chloride was prepared from 5-(2-ethoxyphenyl)-3-n-propyl-1,6-dihydro-7H-pyrazolo[4,3-d]pyrimidin-7-one following the procedure of Example 102 and was obtained as a white solid (78%). Rf 0.25 (silica; ether).

It was used without further purification.

EXAMPLE 135

5-[2-Ethoxy-5-(4-methylpierazinyl)sulphonylphenyl]-3-n-propyl-1,6-dihydro-7H-pyrazolo[4,3-d]pyrimidin-7-one The title sulphonamide was prepared from 5-(5-chlorosulphonyl-2-ethoxyphenyl)-3-n-propyl-1,6-dihydro-7H-pyrazolo[4,3-d]pyrimidin-7-one following the procedure of Example 103 and was obtained as a white solid (70%), m.p. 236–239° C. Found: C, 54.84; H, 6.27; N, 18.10. $C_{21}H_{28}N_6O_4S$ requires C, 54.76; H, 6.13; N, 18.25%.

EXAMPLE 136

3-Bromomethyl-5-chloro-1-methyl-4-nitropyrazole

N-Bromosuccinimide (10.7 g, 60.0 mmol) was added to a solution of 5-chloro-1,3-dimethyl-4-nitropyrazole (8.78) g, 50.0 mmol) in carbon tetrachloride (100 ml) and the solution was heated under reflux whilst being irradiated with visible light (150 W tungsten lamp) for 3 days. At intervals throughout the reaction, quantities of benzoyl peroxide (6×50 mg) were added. The solvent was removed by evaporation under vacuum and the residue chromatographed on silica gel eluting with a 1:1 mixture of dichloromethane and hexane to give the bromide as an off-white solid (8.0 g, 63%), m.p. 80–82° C. Found: C, 23.95; H, 2.05; N, 16.31. $C_5H_5BrClN_3O_2$ requires C, 23.60; H, 1.98; N, 16.51%.

EXAMPLE 137

5-Chloro-3-methoxymethyl-1-methyl-4-nitropyrazole

A solution of 3-bromomethyl-5-chloro-1-methyl-4-nitropyrazole (5.0 g, 19.6 mmol) in methanol (50 ml) was treated with silver nitrate (5.75 g, 33.8 mmol) and the mixture heated under reflux for 2 hours. The cooled reaction mixture was filtered and the filtrate evaporated under vacuum. The residue was partitioned between ethyl acetate (100 ml) and water (50 ml) and the aqueous phase extracted with a further quantity of ethyl acetate (50 ml). The organic extracts were combined, dried ($MgSO_4$) and evaporated under vacuum. Chromatography on silica gel, eluting with a 97:3 mixture of dichloromethane and methanol, gave the title pyrazole as a white solid (1.6 g, 40%), m.p. 59–63° C. Found: C, 34.65; H, 3.83; N, 20.05. $C_6H_8ClN_3O_3$ requires C, 35.05; H, 3.92; N, 20.44%.

EXAMPLE 138

5-Cyano-3-methoxymethyl-1-methyl-4-nitropyrazole

A solution of 5-chloro-3-methoxymethyl-1-methyl-4-nitropyrazole (205 mg, 1.0 mmol), potassium cyanide (130 mg, 2.0 mmol) and 18-crown-6 (10 mg) in acetonitrile (2 ml) was heated under reflux overnight. The solvent was evaporated under vacuum and the residue partitioned between ethyl acetate (20 ml) and water (20 ml). The organic phase was separated, dried ($MgSO_4$) and evaporated under vacuum, then the residue chromatographed on silica gel eluting with a 1:1 mixture of ethyl acetate and pentane. Trituration of the crude product with ether provided a yellow solid (38 mg, 19%), m.p. 48–50° C. Found: C, 42.89; H, 4.15; N, 28.78. $C_7H_8N_4O_3$ requires C, 42.86; H, 4.11; N, 28.56%.

EXAMPLE 139

4-Amino-5-cyano-3-methoxymethyl-1-methylpyrazole

The title compound was prepared from 5-cyano-3-methoxymethyl-1-methyl-4-nitropyrazole following the procedure of Example 99 and was obtained as an off-white solid (68%), m.p. 82–84° C. Found: C, 50.81; H, 6.13; N, 33.94. $C_4H_{10}N_4O$ requires C, 50.59; H, 6.07; N, 33.72%.

EXAMPLE 140

5-Cyano-4-(2-ethoxybenzamido)-3-methoxymethyl-1-methylpyrazole

The title compound was prepared from 4-amino-5-cyano-3-methoxymethyl-1-methylpyrazole following the procedure of Example 100 and was obtained as an off-white solid (61%), m.p. 103–105° C. Found: C, 61.21; H, 5.98; N, 17.80. $C_{16}H_{18}N_4O_3$ requires C, 61.13, H, 5.77; N, 17.83%.

EXAMPLE 141

5-(2-Ethoxyphenyl)-3-methoxymethyl-1-methyl-1,6-dihydro-7H-pyrazolo[4,3-d]pyrimidin-7-one The title compound was prepared from 5-cyano-4-(2-ethoxybenzamido)-3-methoxymethyl-1-methyl-pyrazole following the procedure of Example 101, via in situ generation of the 5-primary amide derivative, and was obtained as a white solid (38%), m.p. 160–161° C. Found: C, 61.35; H, 5.75; N, 17.98. $C_{16}H_{18}N_4O_3$ requires C, 61.13; H, 5.77; N, 17.83%.

EXAMPLE 142

3-Methoxymethyl-1-methyl-5-[5-(4-methylpiperazinylsulphonyl)-2-ethoxyphenyl]1,6-dihydro-7H-pyrazolo[4,3-d]pyrimidin-7-one 5-(2-Ethoxyphenyl-3-methoxymethyl-1-methyl-1,6-dihydro-7H-pyrazolo[4,3-d]pyrimidin-7-one (470 mg, 1.50 mmol) was dissolved in chlorosulphonic acid (3 ml) at 0° C. The solution was stirred at room temperature for 2 hours, then cautiously added to ice-water (50 ml). The resulting solution was neutralized with saturated sodium carbonate solution, then extracted with a 20:1 mixture of dichloromethane and methanol (2×50 ml). The combined organic extracts were evaporated under vacuum and the residue was dissolved in ethanol (5 ml) and the solution treated with N-methylpiperazine (450 mg, 4.5 mmol). After 1 hour at room temperature the solvent was evaporated under vacuum and the residue chromatographed non-silica gel, eluting with a mixture of dichloromethane, methanol and aqueous ammonium hydroxide solution (90:10:1 by volume). Trituration of the crude product with ethyl acetate gave the title compound as a white solid (49 mg, 7%), m.p. 198–199° C. Found: C, 52.94; H, 6.04; N, 17.67. $C_{21}H_{28}N_6O_5S$ requires C, 52.93; H, 5.92; N, 17.65%.

Also isolated following chromatography and crystallisation from a mixture of ethyl acetate and methanol was 3-hydroxymethyl-1-methyl-5-[5-(4-methylpiperazinylsulphonyl)-2-ethoxyphenyl]-1,6-dihydro-7H-pyrazolo[4,3-d]pyrimidin-7-one as a white solid (51 mg, 7%), m.p. 209–210° C. Found: C, 51.94; H, 5.77; N, 18.05. $C_{20}H_{26}N_6O_5S$ requires C, 51.94; H, 5.67; N, 18.17%.

EXAMPLE 143

1-Ethyl-3-n-propylpyrazole-5-carboxylic acid ethyl ester

This pyrazole was prepared from 3-n-propylpyrazole-5-carboxylic acid ethyl ester and diethyl sulphate, following the procedure described in Example 95, and was obtained as a colourless oil (72%). Rf 0.5 (silica; ethyl acetate, hexane; 1:1).

EXAMPLE 144

1-Ethyl-3-n-propylpyrazole-5-carboxylic acid

This carboxylic acid was prepared from 1-ethyl-3-n-propylpyrazole-5-carboxylic acid ethyl ester, following the procedure described in Example 96, and was obtained as a pale brown solid (89%), m.p. 73–77° C. Found C, 58.62; H, 7.69; N, 15.23. $C_9H_{14}N_2O_2$ requires C, 59.32; H, 7.74; N, 15.37%.

EXAMPLE 145

1-Ethyl-4-nitro-3-n-propylpyrazole-5-carboxylic acid

The title compound was prepared from 1-ethyl-3-n-propylpyrazole-5-carboxylic acid, following the procedure described in Example 97, and was obtained as a colourless solid (96%), m.p. 120–123° C. Found: C, 47.61; H, 5.81; N, 18.54. $C_9H_{13}N_3O_4$ requires C, 47.57; H, 5.77; N, 18.49%.

EXAMPLE 146

1-Ethyl-4-nitro-3-n-propylpyrazole-5-carboxamide

The title amide was prepared from 1-ethyl-4-nitro-3-n-propylpyrazole-5-carboxylic acid, following the procedure described in Example 98, and was obtained as an off-white solid (86%), m.p. 119–120° C. Found: C, 47.38; H, 6.18; N, 24.34. $C_9H_{14}N_4O_3$ requires C, 47.78; H, 6.24; N, 24.77%.

EXAMPLE 147

4-Amino-1-ethyl-3-n-propylpyrazole-5-carboxamide

The title compound was prepared from 1-ethyl-4-nitro-3-n-propylpyrazole-5-carboxamide, by the procedure described in Example 99, and was obtained as an off-white solid (100%), m.p. 93–97° C. Found: C, 55.17; H, 8.34; N, 28.93. $C_9H_{16}N_40$ requires C, 55.08; H, 8.22; N, 28.55%.

EXAMPLE 148

4-(2-Ethoxybenzamido)-1-ethyl-3-n-propylpyrazole-5-carboxamide

The title amide was prepared from 4-amino-1-ethyl-3-n-propylpyrazole-5-carboxamide and 2-ethoxybenzoyl chloride, following the procedure described in Example 100, and was obtained as a colourless solid (73%), m.p. 139–141° C. Found: C, 63.03; H, 7.15; N, 16.50. $C_{18}H_{24}N_4O_3$ requires C, 62.77; H, 7.02; N, 16.27%.

EXAMPLE 149

5- (2-Ethoxyphenyl)-1-ethyl-3-n-propyl-1,6-dihydro-7H-pyrazolo[4,3-d]pyrimidin-7-one The title compound was prepared from 4-(2-ethoxybenzamido)-1-ethyl-3-n-propylpyrazolo-5-carboxamide following the procedure of Example 101, and was obtained as a colourless solid (46%), m.p. 112–114° C. Found: C, 66.59; H, 6.85; N, 17.26. $C_{18}H_{22}N_4O_2$ requires C, 66.23; H, 6.79; N, 17.17%.

EXAMPLE 150

5-(5-Chlorosulphonyl-2-ethoxyphenyl)-1-ethyl-3-n-propyl-1,6-dihydro-7H-pyrazolo[4,3-d]pyrimidin-7-one The title compound was prepared from 5-(2-ethoxyphenyl)-1-ethyl-3-n-propyl-1,6-dihydro-7H-pyrazolo[4,3-d]pyrimidin-7-one following the procedure of Example 102, and was obtained as a methylene chloride solvate (86%), m.p. 170–172° C. Found: C, 49.82; H, 4.84; N, 12.77. $C_{18}H_{21}ClN_4O_4S$; ⅙ $CH_2Cl_2$ requires C, 49.70; H, 4.90; N, 12.77%.

EXAMPLE 151

5-[2-Ethoxy-5-(4-methylpiperazinylsulphonyl)phenyl]-1-ethyl-3-n-propyl-1,6-dihydro-7H-pyrazolo[4,3-d]pyrimidin-7-one The title sulphonamide was prepared from 5-(5-chlorosulphonyl-2-ethoxyphenyl)-1-ethyl-3-n-propyl-1,6-dihydro-7H-pyrazolo[4,3-d]pyrimidin-7-one and N-methylpiperazine following the procedure of Example 103 and was obtained as a colourless solid (43%), m.p. 160–162° C. Found: C, 57.24; H, 6.17; N, 16.83. $C_{23}H_{32}N_6O_4S$ requires C, 56.54; H, 6.60; N, 17.20%. Rf 0.35 (silica; dichloromethane, methanol; 9:1).

EXAMPLE 152

5-{2-Ethoxy-5-[4-(2-hydroxyethyl)piperazinylsulphonyl]phenyl}-1-ethyl-3-n-propyl-1,6-dihydro-7H-pyrazolo[4,3-d]pyrimidin-7-one The title sulphonamide was prepared from 5-(5-chlorosulphonyl-2-ethoxyphenyl)-1-ethyl-3-n-propyl-1,6-dihydro-7H pyrazolo[4,3-d]pyrimidin-7-one and N-(2-hydroxyethyl)piperazine following the procedure of Example 103 and was obtained as a colourless solid (88%), m.p. 191–193° C. Found: C, 55.74; H, 6.55; N, 15.78. $C_{24}H_{34}N_6O_5S$ requires C, 55.58; H, 6.61; H, 16.20%.

EXAMPLE 153

Derivatives of 2-phenyl-8-azapurinone, such as 2-(o-propoxyphenyl)-8-azapurin-6-one, may be prepared from the appropriate benzamidine by the synthetic route outlined below in Scheme I. The intermediates may be used, in many cases, in subsequent stages without purification.

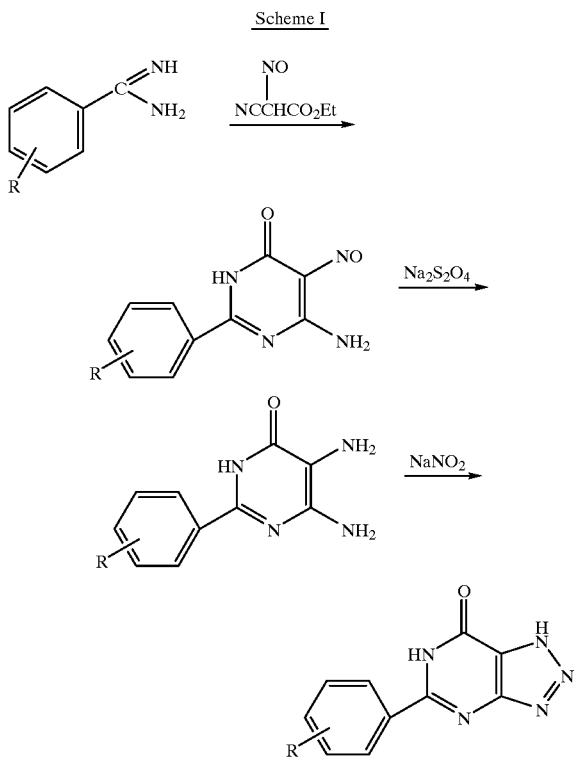

In particular variance to this Scheme I, 2-(2-hydroxyphenyl)-8-azapurin-6-one was prepared by hydrogenolysis of 2-(2-benzyloxyphenyl)-8-azapurinone using 5% Pd/c at atmospheric pressure and room temperature. 2-(2-ammophenyl)-8-azapurinone was prepared by hydrolysis of a 2-(2-Tsulphonamidophenyl)-8-azapurinone according to the method of G. W. H. Cheeseman, J. Chem. Soc., 3308 (1955).

EXAMPLE 154

Pharmaceutical compositions for oral administration are prepared by combining the following:

|  | % w/w | | |
| --- | --- | --- | --- |
| 2-(2-Propoxyphenyl)thieno[2,3-d]pyrimidin-4(3H)-one | 0.5 | 8.0 | 7.14 |
| 2% w/w Soya lecithin in soya bean oil | 90.45 | 88.2 | 84.41 |
| Hydrogenated vegetable shortening and beeswax | 9.05 | 8.8 | 8.45 |

The formulations are then filled into individual soft gelatin capsules.

EXAMPLE 155

A pharmaceutical composition for parenteral administration is prepared by dissolving the title compound of Example 4 (0.02 g) in polyethylene glycol 300 (25 ml) with heating. This solution is then diluted with water for injections Ph. Eur. (to 100 ml). The solution is then sterilised by filtration through a 0.22 micron membrane filter and sealed in sterile containers.

PREPARATION 1

5-Amino-1-n-propylpyrazole-4-carboxamide

A solution of 5-amino-4-cyano-1-n-propylpyrazole (J. Med. Chem., 1968, 11, 79; 4.0 g, 0.0027 mol) in a mixture of concentrated sulphuric acid (30 ml) and water (3 ml) was heated at 90° C. for 1 hour. The cool reaction mixture was poured into ice/water (70 g) and the resulting mixture basified with solid sodium carbonate to pH 8. The aqueous solution thus obtained was extracted with ethyl acetate (5×100 ml), the combined extracts dried ($Na_2SO_4$) and the solvent removed by evaporation under vacuum to give the title compound as a pale yellow solid (4.25 g, 95%). A sample was obtained as colourless crystals, m.p. 183–185° C., by crystallisation from methanol-diethyl ether. Found: C, 50.39; H, 6.94; N, 33.21. $C_7H_{12}N_4O$ requires C, 49.99; H, 7.19; N, 33.31%.

PREPARATION 2

5-(2-Ethoxybenzamido)-1-n-propylpyrazole-4-carboxamide

2-Ethoxybenzoyl chloride (0.73 g, 0.0039 mol) was added dropwise to a solution of 5-amino-1-n-propylpyrazole-4-carboxamide (0.56 g, 0.0033 mol) in pyridine (10 ml) and the resulting mixture stirred at room temperature for 20 hours under a dry nitrogen atmosphere. The solvent was removed by evaporation under vacuum and the residue partitioned between dichloromethane (30 ml) and saturated aqueous sodium carbonate solution (30 ml). The organic layer was removed and the aqueous layer extracted with more dichloromethane (2×30 ml). The combined organic extracts were dried ($Na_2SO_4$) and then evaporated under vacuum. The yellow oil thus obtained was purified by column chromatograph ($SiO_2$, 5% MeOH in $CH_2Cl_2$) to give the product as a white solid (0.78 g, 74%). A sample was obtained as colourless crystals, m.p. 155–157° C., by crystallisation from ethyl acetate-methanol. Found: C, 60.98; H, 6.45; N, 17.78. $C_{16}H_2ON_4O_3$ requires C, 60.75; H, 6.37; N, 17.71%.

PREPARATION 3

6-(5-Chlorosulphonyl-2-ethoxyphenyl)-1-n-propyl-1,5-dihydro-4H-pyrazolo[3,4-d]pyrimidin-4-one 6-(2-Ethoxyphenyl)-1-n-propyl-1,5-dihydro-4H-pyrazolo[3,4-d]pyrimidin-4-one (Example 1; 0.5 g, 0.0017 mol) was added portionwise to stirred chlorosulphonic acid (3 ml) at 0° C. and the resulting solution stirred at room temperature for 14 hours. The reaction mixture was then added dropwise to ice/water (20 g) and the aqueous solution thus obtained was extracted with dichloromethane (4×30 ml). The combined extracts were dried ($Na_2SO_4$) and the solvent evaporated under vacuum to give a white solid; trituration with diethyl ether (50 ml) gave the title compound (0.67 g, 100%), m.p. 177–180° C., which was used without further purification.

PREPARATION 4

6-(5-Bromoacetyl-2-ethoxyphenyl)-1-n-propyl-1,5-dihydro-4H-pyrazolo[3,4-d]pyrimidin-4-one Aluminum trichloride (1.34 g, 0.010 mol) was added portionwise to a stirred solution of 6-(2-ethoxyphenyl)-1-n-propyl-1,5-dihydro-4H-pyrazolo[3,4-d]pyrimidin-4-one (Example 13; 1.0 g, 0.0034 mol) and bromoacetyl bromide (1.35, 0.0067 mol) in dichloromethane (30 ml) at 0° C. The reaction solution was allowed to warm to room temperature, stirred for 14 hours, then for a further 2 hours under reflux. The cool reaction mixture was added dropwise to ice/water (50 g) and the resulting mixture stirred for 1 hour. The organic phase was separated and the aqueous phase extracted with dichloromethane (2×50 ml); the combined organic solutions were then washed with brine (10 ml) and dried ($Na_2SO_4$). Removal of the solvent by evaporation under vacuum gave an off-white solid which, when triturated with ether (20 ml) and dried, afforded the product as a white solid (1.29 g, 92%). A sample crystallised from ethyl acetate-hexane as colourless crystals, m.p. 164–166° C. Found: C, 51.88; H, 4.56; N, 13.13. $C_{18}H_{19}BrN_4O_3$ requires C, 51.56; H, 4.57; N, 13.36%.

PREPARATION 5

5-Amino-4-cyano-3-methyl-1-n-propylpyrazole

Sodium methoxide (0.73 g, 0.0135 mol) was added to a suspension of n-propylhydrazine oxalate (1.05 g, 0.0064 mol) in methanol (20 ml) and the mixture stirred for 2 hours at room temperature. (1-Ethoxy-ethylidene)malononitrile (0.88 g, 0.0064 mol) was then added portionwise over 10 minutes and the resulting mixture was heated under reflux for 4 hours. The reaction mixture was allowed to cool and the solvent removed by evaporation under vacuum. Dichloromethane (20 ml) was added to the residue and, after vigorous stirring of the mixture, the suspension was filtered. The filtrate was evaporated under vacuum and the residue purified by column chromatography ($SiO_2$, 2% MeOH in $CH_2Cl_2$) to give the title compound as pale brown crystals (0.50 g, 48%). A sample crystallised from ethyl acetate as pale brown needles, m.p. 104–105° C. Found: C, 58.82; H, 7.30; N, 34.13. $C_8H_{12}N_4$ requires C, 58.52; H, 7.37; N, 34.12%.

PREPARATION 6

5-Amino-3-methyl-1-n-propylpyrazole-4-carboxamide

By the same method as Preparation 1, the title compound was obtained from 5-amino-4-cyano-3-methyl-1-n-propylpyrazole (2.0 g, 0.012 mol), concentrated sulphuric acid (30 ml) and water (3 ml) as a white solid (2.19 g, 98%). A sample crystallised from methanol-ethyl acetate as colourless crystals, m.p. 165–166° C. Found: C, 53.02; H, 7.87; N, 30.75. $C_8H_{14}N_4O$ requires C, 52.73; H, 7.74; N, 30.75%.

PREPARATION 7

3-Methyl-5-(2-n-propoxybenzamido)-1-n-propylpyrazole-4-carboxamide

The title compound was prepared from 2-n-propoxybenzoyl chloride (5.33 g, 0.027 mol) and 5-amino-3-methyl-1-n-propylpyrazole-4-carboxamide (Preparation 6; 4.07 g, 0.022 mol) in pyridine (100 ml), following the procedure of Preparation 2, and was obtained as a white solid (5.84 g, 76%). A sample was crystallised from ethyl acetate-hexane, m.p. 111–113° C. Found: C, 62.83; H, 7.09; N, 16.26. $C_{18}H_{24}N_4O_3$ requires C, 62.77; H, 7.02; N, 16.27%.

PREPARATION 8

6-(5-Chlorosulphonyl-2-n-propoxyphenyl)-3-methyl-1-n-propyl-1,5-dihydro-4H-pyrazolo[3,4-d]pyrimidin-4-one The title compound was prepared from 3-methyl-6-(2-n-propoxyphenyl)-1-n-propyl-1,5-dihydro-4H-pyrazolo[3,4-d]pyrimidin-4-one (Example 21; 0.5 g, 0.0017 mol) and chlorosulphonic acid (3 ml), by the same procedure as Preparation 3, and was obtained as a white powder (0.587 g, 90%), m.p. 148–150° C. Found: C, 50.88; H, 4.67; N, 13.30. $C_{18}H_{21}ClN_4O_4S$ requires C, 50.88; H, 4.98; N, 13.19%.

PREPARATION 9

2-(2-Propoxyphenyl)-6-purinone

A stirred mixture of 4,5-diamino-2-(2-propoxyphenyl)-pyrimidin-6-one sulphate (1.5 g) (prepared by the addition of concentrated sulphuric acid to an ethanolic solution of the free base) and formamide (15 ml) was heated in an oil bath (temp. 190°–200° C.) for 70 minutes. When cool the mixture was filtered and the collected solid was washed with ethanol to give a crude product 91.1 g), m.p. 254–259° C., which was recrystallised from ethanol to give the title compound, 0.72 g, m.p. 263–265° C.

PREPARATION 10

2-(2-Propoxyphenyl)purine-6,8-dione

A mixture of 4,5-diamino-2-(2-propoxyphenyl)-pyrimidin-6-one (1.3 g), and urea (1.5 g) was heated in an oil bath (temp. 190° C.) for 45 minutes. The resultant solid was digested with hot water, the mixture filtered and the solid washed with water to give a crude product, 1.36 g. Recrystallisation from dimethylformamide gave the title compound (1.01 g), m.p. >350° C., δ(DMSO-$d_6$), 1.01 (t, 3H) ; 1.88 (m, 2H) 4.09 (t, 2H); 7.10, 7.21, 7.52 and 7.76 (multiplets, 4H); about 11.07, 11.55 and 11.95 (very broad singlets, 3H).

PREPARATION 11

1-Methyl-3-n-propylpyrazole-5-carboxylic acid ethyl ester

A mixture of 3-n-propylpyrazole-5-carboxylic acid ethyl ester (24.1 g, 0.132 mol) (prepared by the method of Chem.

Pharm. Bull., 1984, 32, 1568) and dimethyl sulphate (16.8 g, 0.133 mol) were heated to 90° C. for 2.5 hours. The mixture was dissolved in dichloromethane and the solution washed with aqueous sodium carbonate solution. The organic phase was separated, dried ($MgSO_4$) and evaporated under vacuum to give a solid. Chromatography on silica gel (300 g), eluting with dichloromethane, gave the product as a colourless oil (20.4 g, 79%). Rf 0.8 (silica, dichloromethane, methanol, acetic acid; 80:20:1).

PREPARATION 12

1-Methyl-3-n-propylpyrazole-5-carboxylic acid

1-Methyl-3-n-propylpyrazole-5-carboxylic acid ethyl ester (20.2 g, 0.10 mol) was suspended in 6N aqueous sodium hydroxide solution (50 ml, 0.30 mol). The mixture was heated to 80° C. for 2 hours then diluted with water (50 ml) and acidified with concentrated hydrochloric acid (25 ml). Filtration gave the carboxylic acid as pale brown crystals (12.3 g, 71%), m.p. 150–154° C. Found: C,56.99; H,7.25; N,16.90. $C_8H_{12}N_2O_2$ requires C,57.13; H,7.19; N,16.66%.

PREPARATION 13

1-Methyl-4-nitro-3-n-propylpyrazole-5-carboxylic acid

1-Methyl-3-n-propylpyrazole-5-carboxylic acid (12.1 g, 0.072 mol) was added portionwise to a mixture of oleum (13 ml) and fuming nitric acid (11 ml), keeping the temperature below 60° C. After the addition, the mixture was heated at 60° C. overnight and then cooled to room temperature before being poured onto ice; filtration then gave the nitropyrazole as a white solid (11.5 g, 75%), m.p. 124–127° C. Found: C,45.43; N,5.22; N,19.42. $C_8H_{11}N_3O_4$ requires C,45.57; H,5.20; N,19.71%.

PREPARATION 14

1-Methyl-4-nitro-3-n-propylpyrazole-5-carboxamide

1-Methyl-4-nitro-3-n-propylpyrazole-5-carboxylic acid (11.3 g, 0.053 mol) was added to thionyl chloride (50 ml) and the resulting mixture heated under reflux for 3 hours. The reaction mixture was then cooled and excess thionyl chloride removed by evaporation under vacuum. The oily residue was dissolved in acetone (50 ml) and the solution cautiously added to a mixture of ice (50 g) and concentrated aqueous ammonium hydroxide solution (50 ml). The precipitate was collected by filtration to provide the pyrazole-carboxamide as a pale yellow solid (8.77 g, 78%), m.p. 141–143° C. Found: C,45.22; H,5.71; N,26.12. $C_8H_{12}N_4O_3$ requires C,45.28; H,5.70; N,26.40%.

PREPARATION 15

4-Amino-1-methyl-3-n-propylpyrazole-5-carboxamide

1-Methyl-4-nitro-3-n-propylpyrazole-5-carboxamide (3.45 g, 16.2 mmol) and stannous chloride dihydrate (18.4 g, 81 mmol) were suspended in ethanol and the mixture heated under reflux for 2 hours. The resulting solution was cooled to room temperature, basified to pH 9 by the addition of 2N aqueous sodium hydroxide solution and extracted with dichloromethane (3×150 ml). The organic extracts were combined, dried ($MgSO_4$) and evaporated under vacuum. Trituration of the residue with ether gave the aminopyrazole as an off-white solid (2.77 g, 94%), m.p.; 98–101° C. Found: C,52.84; H,7.81; N,30.38. $C_8H_{14}N_4O$ requires C,52.73; H,7.74; N,30.75%.

PREPARATION 16

4-(2-Ethoxybenzamido)-1-methyl-3-n-propylpyrazole-5-carboxamide

A solution of 2-ethoxybenzoyl chloride (6.1 g, 33.0 mmol) in dichloromethane (50 ml) was added to a stirred solution of 4-amino-1-methyl-3-n-propylpyrazole-5-carboxamide (3.0 g, 16.4 mmol), 4-dimethylaminopyridine (0.02 g, 0.164 mmol) and triethylamine (3.34 g, 33.0 mmol) in dichloromethane (50 ml) at 0° C. The resulting mixture was allowed to warm to room temperature and stirred for a further 2 hours. The solvent was evaporated under vacuum, the residue dissolved in a 19:1 mixture of dichloromethane and methanol (250 ml), and then the solution washed with 1N hydrochloric acid (100 ml), dried ($MgSO_4$) and evaporated under vacuum. The crude material was chromatographed on silica gel (200 g), eluting with a 97:3 mixture of dichloromethane and methanol, to give a pink solid; crystallisation from ethyl acetate-hexane gave the pyrazole-5-carboxamide as a pale pink solid (2.2 g, 40%), m.p. 153–155° C. Found: C,61.66; H,6.77; N,16.95. $C_{17}H_{22}N_4O_3$ requires C,61.80; H,6.71; N,16.96%.

PREPARATION 17

5-(2-Ethoxyphenyl)-1-methyl-3-n-propyl-1,6-dihydro-7H-pyrazolo[4,3-d]pyrimidin-7-one 4-(2-Ethoxybenzamido)-1-methyl-3-n-propylpyrazole-5-carboxamide (223 g, 0.676 mol) was added portionwise to a solution of sodium hydroxide (54 g, 1.35 mol) and 30% hydrogen peroxide solution (224 ml) in water (2000 ml). Ethanol (700 ml) was added and the resulting mixture heated under reflux for 2.5 hours, cooled, then evaporated under vacuum. The resulting solid was treated with 2N hydrochloric acid (380 ml), with external cooling, and the mixture was extracted with dichloromethane (1×700 ml; 3×200 ml). The combined organic extracts were washed successively with saturated aqueous sodium carbonate solution (3×400 ml) and brine (300 ml), then dried ($Na_2SO_4$) and evaporated under vacuum.

Chromatography of the residue on silica gel (1000 g), using a methanol in dichloromethane elution gradient (0–1% methanol), followed by trituration of the crude product with ether (300 ml), gave the title compound as a colourless solid (152.2 g, 72%), m.p. 143–146° C. Found: C,65.56; H,6.44; N,18.14. $C_{17}H_{20}N_4O_2$ requires C,65.36; H,6.45; N,17.94%.

PREPARATION 18

5-(5-Bromoacetyl-2-ethoxyphenyl)-1-methyl-3-n-propyl-1,6-dihydro-7H-pyrazolo[4,3-d]-pyrimidin-7-one Aluminum trichloride (12.8 g, 0.096 mol) was added portionwise over 1 hour to a stirred solution of 5-(2-ethoxyphenyl)-1-methyl-3-n-propyl-1,6-dihydro-7H-pyrazolo[4,3-d]pyrimidin-7-one (10.0 g, 0.032 mol) and bromoacetyl bromide (5.6 ml, 0.064 mol) in dichloromethane (150 ml) at 0° C. After 18 hours at room temperature, the reaction mixture was poured into ice and water (400 g) and the resulting mixture stirred vigorously. The organic phase was separated and the aqueous phase further extracted with dichloromethane (2×100 ml). The organic solutions were combined, dried ($Na_2SO_4$) and evaporated under vacuum to give an off-white solid, trituration of which from ether gave the title compound as a white solid (10.87 g, 78%), m.p. 159–160° C. Found: C,52.54; H,4.88; N,12.78. $C_{19}H_{21}BrN_4O_3$ requires C,52.67; H,4.88; N,12.93%.

PREPARATION 19

1-Methyl-4-(2-n-propoxybenzamido)-3-n-propylpyrazole-5-carboxamide

This amide was prepared from 2-n-propoxybenzoyl chloride following the procedure described in Preparation 16 and was obtained as a pink solid (63%), m.p. 148–149° C. Found: C,62.97; H,7.00; N,16.29. $C_{18}H_{24}N_4O_3$ requires C,62.77; H,7.02; N,16.27%.

PREPARATION 20

1-Methyl-S-(2-n-propoxyphenyl)-3-n-propyl-1,6-dihydro-7H-pyrazolo[4,3-d]pyrimidin-7-one 1-Methyl-4-(2-n-propoxybenzamido)-3-n-propylpyrazole-5-carboxamide(0.34 g, 0.99 mmol) was added to a stirred mixture of 30% hydrogen peroxide solution (1.0 ml), potassium carbonate (0.54 g, 3.92 mmol), water (10 ml) and ethanol (5 ml). The mixture was heated under reflux for 38 hours and then evaporated under vacuum. The residue was suspended in water (20 ml), then the suspension acidified with 2N hydrochloric acid and extracted with dichloromethane (3×20 ml). The extracts were combined, dried ($Na_2SO_4$) and evaporated under vacuum. The resulting residue was chromatographed on silica gel (6 g), using a methanol in dichloromethane elution gradient (0–1% methanol), to give an oil, successive trituration of which with ether gave the required product as a white solid (0.19 g, 59%), m.p. 111–114° C. Found: C,66.26; H,6.92; N,17.15. $C_{18}H_{22}N_4O_2$ requires C,66.23; H,6.80; N,17.17%.

PREPARATION 21

5-(5-Bromoacetyl-2-n-propoxyphenyl)-1-methyl-3-n-propyl-1,6-dihydro-7H-pyrazolo[4,3-d]pyrimidin-7-one Aluminum trichloride (6.0 g, 0.045 mol) was added portionwise to a stirred solution of 1-methyl-5-(2-n-propoxyphenyl)-3-n-propyl-1,6-dihydro-7H-pyrazolo[4,3-d]pyrimidin-7-one(5.0 g, 0.0153 mol) and 2-bromoacetyl chloride (2.5 ml, 0.0303 mol) in dichloromethane (100 ml) at 0° C. The reaction mixture was allowed to warm to room temperature, stirred for 18 hours, heated under reflux for 3 hours and then added cautiously to ice and water (100 g). The resulting mixture was stirred for 1 hour and extracted with dichloromethane (2×50 ml). The combined organic extracts were washed with brine (2×50 ml), dried ($Na_2SO_4$), then evaporated under vacuum to give an off-white solid, which was triturated with ether to give the title compound as a white solid (4.1 g, 60%). A small sample was crystallised from ethyl acetate-hexane to give the pure product, m.p. 136–137° C. Found: C,53.82; H,5.24; N,12.57. $C_{20}H_{23}BrN_4O_3$ requires C,53.70; H,5.18; N,12.52%.

PREPARATION 22

5-Acetyl-2-ethoxybenzoic acid methyl ester

Iodoethane (16.4 g, 0.105 mol) was added to a stirred mixture of 5-acetyl-2-hydroxybenzoic acid methyl ester (10 g, 51.5 mol) and anhydrous potassium carbonate (14.4 g, 0.104 mol) in 2-butanone (200 ml) and the resulting mixture heated under reflux for 3 days. The solvent was removed by evaporation under vacuum and the residue partitioned between water (100 ml) and ethyl acetate (100 ml). The aqueous phase was removed and extracted with further ethyl acetate (4×100 ml). The organic solutions were combined, dried ($Na_2SO_4$) and evaporated under vacuum. The residue was chromatographed on silica gel (130 g), using a methanol in dichloromethane elution gradient (0–1% methanol), to give the title compound as colourless crystals (10.15 g, 89%), m.p. 50–55° C. Found: C,64.88; H,6.38. $C_{12}H_{14}O_4$ requires C,64.85; H,6.35%.

PREPARATION 23

5-Acetyl-2-ethoxybenzoic acid

A mixture of 5-acetyl-2-ethoxybenzoic acid methyl ester (9.6 g, 0.043 mol), 5M aqueous sodium hydroxide solution (44 ml, 0.217 mol), water (80 ml) and 1,4-dioxan (80 ml) was stirred at room temperature for 18 hours. The solvent was removed by evaporation under vacuum, the residue dissolved in water (100 ml) and the resulting solution acidified to pH 1 with concentrated hydrochloric acid. The aqueous mixture was extracted with ethyl acetate (4×100 ml) and the combined extracts dried ($Na_2SO_4$) and evaporated under vacuum. The resulting solid was crystallised from ethyl acetate to give the title compound as a colourless solid (5.4 g, 60%), m.p. 122–125° C. Found: C,63.20; H,5.81. $C_{11}H_{12}O_4$ requires C,63.45; H,5.81%.

PREPARATION 24

5-Acetyl-2-ethoxybenzoyl chloride

Oxalyl chloride (3.66 g, 0.029 mol) was added dropwise to a stirred solution of 5-acetyl-2-ethoxybenzoic acid (3.0 g, 0.014 mol) in dichloromethane (15 ml) and dimethylformamide (0.1 ml). After 3 hours at room temperature, the solvent was removed by evaporation under vacuum and the residue azeotroped with hexane (3×30 ml) to give the title compound, which was used without further purification.

PREPARATION 25

4-(5-Acetyl-2-ethoxybenzamido)-1-methyl-3-n-propylpyrazole-5-carboxamide

The title compound was prepared from 5-acetyl-2-ethoxybenzoyl chloride and 4-amino-1-methyl-3-n-propylpyrazole-5-carboxamide following the procedure of Preparation 6, and was obtained as a white solid (60%), m.p. 225–227° C. Found: C,61.35; H,6.25; N,15.07. $C_{19}H_{24}N_4O_4$ requires C,61.28; H,6.50; N,15.04%.

PREPARATION 26

5-(5-Chloromethyl-2-n-propoxyphenyl)-1-methyl-3-n-propyl-1,6-dihydro-7H-pyrazolo-[4,3-d]pyrimidin-7-one 1-Methyl-5-(2-n-propoxyphenyl)-3-n-propyl-1,6-dihydro-7H-pyrazolo[4,3-d]pyrimidin-7-one (0.80 g, 0.00246 mol) was added portionwise to stirred concentrated hydrochloric acid (10 ml) at room temperature. Paraformaldehyde (0.20 g, 0.00246 mol) was then added and the resulting solution stirred at 120° C. for 22 hours. The reaction mixture was cooled and poured into ice and water (50 g), then the resulting mixture extracted with ethyl acetate (3×30 ml). The organic extracts were combined, dried ($Na_2SO_4$) and evaporated under vacuum to give a white solid. Trituration with ether, followed by crystallisation from ethyl acetate-hexane, gave the title compound as colourless crystals (0.65 g, 70%), m.p. 102–104° C. Found: C,60,91; H,6.14; N,14.94. $C_{19}H_{23}ClN_4O_2$ requires C,60.88; H,6.18; N,14.95%.

PREPARATION 27

5-(2-Ethoxy-5-nitrophenyl)-1-methyl-3-n-propyl-1,6-dihydro-7H-pyrazolo[4,3-d]pyrimidin-7-one Concentrated nitric acid (0.5 ml) was added dropwise to a stirred solution of 5-(2-ethoxyphenyl)-1-methyl-3-n- propyl-1.6-dihydro-7H-pyrazolo[4,3-d]pyrimidin-7-one (2.0 g, 0.0064 mol) in concentrated sulphuric acid (10 ml) at 0° C., and the resulting orange solution was stirred at room temperature for 18 hours. The reaction solution was then added dropwise to stirred ice and water (200 g) and the solid precipitate collected by filtration. This solid was then dissolved in dichloromethane (50 ml) and the solution washed successively with brine (2×30 ml) and water (30 ml), dried ($Na_2SO_4$) and evaporated under vacuum to give a yellow solid. Crystallisation from acetonitrile gave the title compound as yellow needles (1.40 g, 61%), m.p. 214–216° C. Found: C,57.35; H,5.21; N,19.49. $C_{17}H_{19}N_5O_4$ requires C,57.13; H,5.36; N,19.60%.

PREPARATION 28

5-(5-Amino-2-ethoxyphenyl)-1-methyl-3-n-propyl-1,6-dihydro-7H-pyrazolo[4,3-d]pyrimidin-7-one 5-(2-Ethoxy-5-nitrophenyl)-1-methyl-3-n-propyl-1,6-dihydro-7H-pyrazolo[4,3-d]pyrimidin-7-one (0.64 g, 0.0018 mol) was dissolved in ethanol (50 ml) and the solution stirred with 5% palladium on charcoal catalyst (0.050 g) under hydrogen at room temperature and 50 p.s.i. pressure for 4 hours. The mixture was filtered to remove the catalyst, the filtrate evaporated under vacuum, and the residue triturated with ether to give the title compound as an off-white solid (0.56 g, 95%), m.p. 147–148° C. Found: C,62.63; H,6.60; N,21.57. $C_{17}H_{21}N_5O_2$ requires C,62.36; H,6.47; N, 21.39%.

PREPARATION 29

4-Benzyl-1-piperazinylsulphonyl chloride

A solution of 1-benzylpiperazine (20.0 g, 0.114 mol) in acetonitrile (45 ml) was added to a solution of sulphuryl chloride (28 ml, 0.346 mol) in acetonitrile (50 ml) and the mixture heated under reflux for 17 hours, then cooled. The solvent was removed by evaporation under vacuum, then the residue triturated with either (20×50 ml) to yield the title compound (27.8 g, 89%), which was used without further purification.

BIOLOGICAL EFFECTS

Compound No. 2-(o-propoxyphenyl)-8-azapurin-6-one was assayed for its effect on the human colon carcinoma cell line, HT-29 obtained from ATCC, (Rockville, Md.) to ascertain the degree of growth inhibition. Growth inhibition of this cell line is thought to be indicative of a benefit on precancerous lesions and neoplasms. The cell line and growth assay employed for these experiments is well characterized, and is used by the United States National Cancer Institute in its screening program for new anti-cancer drugs.

Drug stock solutions were made in 100% DMSO then diluted with RPMI media for cell culture testing. All drug solutions were prepared fresh on the day of testing. The cultured cells were obtained at passage #118 and grown in RPMI media supplemented with 5% fetal calf serum, and 2 mM glutamine, 100 U/ml penicillin, 100 U/ml streptomycin, and 0.25 μg/ml amphotericin. The cultures were maintained in a humidified atmosphere of 95% air and 5% $CO_2$ at 37° C. The cultures were passaged at preconfluent densities using a solution of 0.05% trypsin and 0.53 mM EDTA. All experiments involved HT-29 cells between passages 120 and 140. Cells were plated at the following densities to obtain cultures used for the experiments: 500 cells/well for 96 well flat-bottom microtiter plates, $1 \times 10^6$ cells per 25 $cm^2$ flask, or $4 \times 10^6$ cells per 75 $cm^2$ flask.

Apoptosis and necrosis were measured using an assay which allowed for the simultaneous measurement of both types of cell death based on morphological characteristics of apoptotic cells (i.e., condensed chromatin) and membrane permeability. Drug preparation and cell culture conditions were the same as above. Confluent cultures were assayed for apoptosis and necrosis by fluorescent microscopy following labeling with acridine orange and ethidium bromide. Floating and attached cells were collected by trypsinization and washed three times in PBS. One ml aliquots of $1 \times 10^6$ cells were centrifuged (300 g). The pellet was resuspended in 25 μl media and 1 μl of a dye mixture containing 100 μg/ml acridine orange and 100 μg/ml llethidium bromide prepared in PBS and mixed gently. Ten μl of mixture was placed on a microscope slide and covered with a 22 $mm^2$ coverslip and examined under 40× dry objectives using epilumination and filter combination.

An observer blinded to the identity of the treatments scored at least 100 cells per sample. Apoptotic cells were identified by nuclear condensation of chromatin stained by the acridine orange or ethidium bromide. Necrotic cells were identified by uniform labeling of the cell with ethidium bromide. These results are provided below.

TABLE 1

Apoptosis and Necrosis Effects for 2-(2-propoxyphenyl)-8-azapurin-6-one

| Treatment Cells | % Apoptotic Cells | % Necrotic |
|---|---|---|
| None | 7 | 5 |
| Vehicle | 9 | 2 |
| Compound (40 μM) | 30 | 2 |
| Compound (36 μM) | 37 | |

Data was also obtained, under the same procedure above, for the percent of apoptotic cells induced by treatment with varying concentrations of the same compound, which is described in Example 153. These results are provided in Table 2 below.

TABLE 2

Apoptosis vs. Varying Concentrations of 2-(2-propoxyphenyl)-8-azapurin-6-one

| Drug Concentration (μM) | % Apoptotic Cells |
|---|---|
| 0 | 16 |
| 1 | 8 |
| 5 | 9 |
| 10 | 14 |
| 25 | 48 |
| 50 | 37 |

It will be understood that various changes modifications can be made in the details of procedure, formulation and use without departing from the spirit of the invention, especially as defined in the following claims.

We claim:

1. A method of treating a patient having precancerous lesions in need of treatment wherein the precancerous lesions are sensitive to a compound below, comprising administering to the patient a pharmacologically effective amount of a compound of the formula:

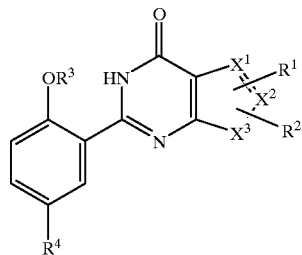

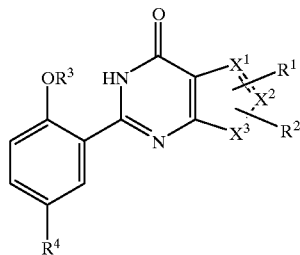

wherein

R¹ is H; $C_1$–$C_3$ alkyl, $C_1$–$C_3$ alkyl substituted with one or more fluoro substituents; or $C_3$–$C_5$ cycloalkyl;

R₂ is H, $C_1$–$C_6$ alkyl, or $C_1$–$C_6$ alkyl substituted with one or more fluoro substituents or with $C_3$–$C_6$ cycloalkyl;

R₃ is $C_1$–$C_6$ alkyl; $C_1$–$C_6$ alkyl substituted with one or more fluoro substituents or with $C_3$–$C_6$ cycloalkyl; $C_3$–$C_5$ cycloalkyl; $C_3$–$C_6$ alkenyl; or $C_3$–$C_6$ alkynyl;

R₄ is $C_1$–$C_4$ alkyl; $C_1$–$C_4$ alkyl substituted with OH, $NR^5R^6$, CN, $CONR^5R^6$, $SO_2NR^5R^6$, or $CO_2R^7$; $C_2$–$C_4$ alkenyl; $C_2$–$C_4$ alkenyl substituted with CN, $CONR^5R^6$ or $CO_2R^7$; $C_2$–$C_4$ alkanoyl; $C_2$–$C_4$ alkanoyl substituted with $NR^5R^6$; hydroxy $C_2$–$C_4$ alkyl; hydroxy $C_2$–$C_4$ alkyl substituted with $NR^5R^6$; ($C_2$–$C_3$ alkoxy) $C_1$–$C_2$ alkyl; ($C_2$–$C_3$ alkoxy)$C_1$–$C_2$ alkyl substituted with OH or $NR^5R^6$; CH=CHCN; CH=CHCONR⁵R⁶; CH=CHCO₂R⁷; CONR⁵R⁶; CO₂R⁷; halo; NR⁵R⁶; NHSO₂NR⁵R⁶; NHSO₂R⁸; phenyl or phenyl substituted with methyl; or pyridyl or imidazolyl either of which is substituted with H or methyl;

R⁵ and R⁶ are each independently H or $C_1$–$C_4$ alkyl, or together with the nitrogen atom to which they are attached form a 4-(NR⁹)piperazinyl group wherein said group is substituted with H, $C_1$–$C_4$ alkyl or hydroxy;

R⁷ is H or $C_1$–$C_4$ alkyl;

R⁸ is $C_1$–$C_3$ alkyl or $C_1$–$C_3$ alkyl substituted with NR⁵R⁶; and

R⁹ is H; $C_1$–$C_3$ alkyl or $C_1$–$C_3$ alkyl substituted with phenyl; hydroxy $C_2$–$C_3$ alkyl; or $C_1$–$C_4$ alkanoyl or pharmaceutically acceptable salts thereof; and X¹, X² and X³ may be independently nitrogen or carbon with the proviso that: at least two of X¹, X² and X³ must be nitrogen.

2. The method of claim 1 wherein R² and R⁴ are hydrogen, R³ is lower alkyl, and X¹ and X³ are nitrogen.

3. The method of claim 1 wherein R¹ is hydrogen and X¹, X² and X³ are nitrogen.

4. The method of claim 3 wherein the compound is 2-(2-propoxyphenyl)-8-azapurinone.

5. A method for inhibiting the growth of neoplastic cells sensitive to a compound below, comprising exposing said cells to an effective amount of a compound of formula:

wherein

R¹ is H; $C_1$–$C_3$ alkyl, $C_1$–$C_3$ alkyl substituted with one or more fluoro substituents; or $C_3$–$C_5$ cycloalkyl;

R₂ is H, $C_1$–$C_6$ alkyl, or $C_1$–$C_6$ alkyl substituted with one or more fluoro substituents or with $C_3$–$C_6$ cycloalkyl;

R₃ is $C_1$–$C_6$ alkyl; $C_1$–$C_6$ alkyl substituted with one or more fluoro substituents or with $C_3$–$C_6$ cycloalkyl; $C_3$–$C_5$ cycloalkyl; $C_3$–$C_6$ alkenyl; or $C_3$–$C_6$ alkynyl;

R₄ is $C_1$–$C_4$ alkyl; $C_1$–$C_4$ alkyl substituted with OH, NR⁵R , CN, CONR⁵R⁶, SO₂NR⁵R⁶, or CO₂R⁷; $C_2$–$C_4$ alkenyl; $C_2$–$C_4$ alkenyl substituted with CN, CONR⁵R⁶ or CO₂R⁷; $C_1$–$C_4$ alkanoyl; $C_2$–$C_4$ alkanoyl substituted with NR⁵R ⁶; hydroxy $C_1$–$C_4$ alkyl; hydroxy $C_2$–$C_4$ alkyl substituted with NR⁵R ⁶; ($C_2$–$C_3$ alkoxy) $C_1$–$C_2$ alkyl; ($C_2$–$C_3$ alkoxy)$C_1$–$C_2$ alkyl substituted with OH or NR⁵R⁶; CH=CHCN; CH=CHCONR⁵R⁶; CH=CHCO₂R⁷; CONR⁵R⁶; CO₂R⁷; halo; NR⁵R⁶; NHSO₂ NR⁵R⁶; NHSO₂R⁸; phenyl or phenyl substituted with methyl; or pyridyl or imidazolyl either of which is substituted with H or methyl;

R⁵ and R⁶ are each independently H or $C_1$–$C_4$ alkyl, or together with the nitrogen atom to which they are attached form a 4-(NR⁹)piperazinyl or group wherein said group is substituted with H, $C_1$–$C_4$ alkyl or hydroxy;

R⁷ is H or $C_1$–$C_4$ alkyl;

R⁸ is $C_1$–$C_3$ alkyl or $C_1$–$C_3$ alkyl substituted with NR⁵R⁶; and

R⁹ is H; $C_1$–$C_3$ alkyl or $C_1$–$C_3$ alkyl substituted with phenyl; hydroxy $C_2$–$C_3$ alkyl; or $C_1$–$C_4$ alkanoyl; or pharmaceutically acceptable salts thereof: and X¹, X² and X³ may be independently nitrogen or carbon with the proviso that: at least two of X¹, X² and X³ must be nitrogen.

6. The method of claim 5 wherein R² and R⁴ are hydrogen, R³ is lower alkyl, and at least X¹ and X³ are nitrogen.

7. The method of claim 5 wherein R¹ is hydrogen and X¹, X² and X³ are nitrogen.

8. The method of claim 7 wherein the compound is 2-(2-propoxyphenyl)-8-azapurinone.

* * * * *